United States Patent
Marciano et al.

(10) Patent No.: US 12,344,834 B2
(45) Date of Patent: Jul. 1, 2025

(54) PHYLOGENETIC-BASED DIFFERENTIAL CELL SEPARATION AND DNA EXTRACTION

(71) Applicants: Michael Marciano, Manlius, NY (US); Molly Dunegan, Atlanta, GA (US)

(72) Inventors: Michael Marciano, Manlius, NY (US); Molly Dunegan, Atlanta, GA (US)

(73) Assignee: SYRACUSE UNIVERSITY, Syracuse, NY (US)

(*) Notice: Subject to any disclaimer, the term of this patent is extended or adjusted under 35 U.S.C. 154(b) by 1111 days.

(21) Appl. No.: 17/087,079

(22) Filed: Nov. 2, 2020

(65) Prior Publication Data
US 2021/0171895 A1    Jun. 10, 2021

Related U.S. Application Data

(60) Provisional application No. 62/929,216, filed on Nov. 1, 2019.

(51) Int. Cl.
*C12N 1/06* (2006.01)
*B01L 3/00* (2006.01)

(52) U.S. Cl.
CPC .............. *C12N 1/06* (2013.01); *B01L 3/5021* (2013.01); *B01L 2400/0409* (2013.01)

(58) Field of Classification Search
CPC ..................................................... C12N 1/06
See application file for complete search history.

(56) References Cited

U.S. PATENT DOCUMENTS

2003/0215845 A1* 11/2003 Bille .................. C12N 15/1017
435/270

OTHER PUBLICATIONS

Natarajan et al. "A Modified SDS-Based DNA Extraction Method for High Quality Environmental DNA from Seafloor Environments", Front. Microbiol., Jun. 22, 2016, Sec. Extreme Microbiology, vol. 7—2016 | https://doi.org/10.3389/fmicb.2016.00986 (Year: 2016).*

* cited by examiner

*Primary Examiner* — Ruth A Davis
(74) *Attorney, Agent, or Firm* — David L. Nocilly; Bond, Schoeneck & King PLLC

(57) ABSTRACT

An approach for differentially isolating eukaryotic (plant and animal) DNA from bacterial DNA prior to sequencing using a combination of size exclusion-based separation and differential cell lysis. The method of the present invention exploits the differences of the cellular size and components of each type of organism to be separated. The composition and nature of the cell wall of plant cells, enzymatic sensitivity of bacterial and animal cells and overall size difference of bacterial and plant/animal cells allows one portion of a mixed sample to be lysed while retaining the integrity of the remaining organisms. Separation of one phylogenetic component then permits the remaining components to be extracted with minimal contribution from the preceding component. The separation of DNAs from differing contributing kingdoms in an unknown sample increases interpretability through decreasing complexity in subsequent sequencing applications.

12 Claims, 19 Drawing Sheets

PHYLOGENETIC-BASED DIFFERENTIAL CELL SEPARATION AND DNA EXTRACTION

CROSS-REFERENCE TO RELATED APPLICATIONS

The present application claims priority to U.S. Provisional Application No. 62/929,216, filed on Nov. 1, 2019.

BACKGROUND OF THE INVENTION

1. Field of the Invention

The present invention relates to DNA extraction from samples and, more specifically, to size exclusion and enzymatic separation of bacterial, plant and cells from the kingdom Animalia prior to extraction that maintains cell viability for downstream applications.

2. Description of the Related Art

DNA analyses routinely focus on single organismal targets. However, an unknown biological sample will often contain more biological components rather than just that of the single target organism. While the DNA from non-targeted organisms may contain valuable data regarding the identity of the sample, these non-target organisms can complicate downstream analyses and frustrate the focusing in the single target.

For example, biological samples will contain a mixture of plant, bacterial and eukaryotic DNAs. In forensic analyses, samples taken from a crime scene may include microbial communities that are not the focus of the investigation. For example, a human DNA sample will also contain microbial DNA, and given NGS shotgun sequencing, the shorter and more numerous genomic microbial DNA will likely be preferentially sequenced. This over representation of the non-target DNAs will pose a challenge to the interpretation of results, whereby the target DNAs are not sequenced at appropriate depths.

On the other hand, in medical analyses, samples targeting bacteria populations present may include human tissues. Research involving the human microbiome has proven of the utmost importance for various scientific fields, but the inability to separate the human cells from the plant or bacterial cells has become challenging to researchers and has therefore delayed potentially critical scientific contributions to society.

In either case, the samples contain a wealth of potential information beyond the target, for example, the microbial, plant or animal profiles associated with a person, animal, object or place. Capturing this information is a challenge, however, due to many factors, such as time, cost, and data quality. The reliability and accuracy of environmental DNA NGS data present a more pressing challenge to scientific analysts than cost or time as it is imperative that the data obtained in all aspects of science be accurate and valid. Accordingly, there is a need in the art for an approach that can separate the plant, animal, and bacterial contents of a sample for increased interpretability of any of the contents of the sample.

BRIEF SUMMARY OF THE INVENTION

The present invention comprises a method to differentially isolate eukaryotic (cells from the kingdom Animalia) from plant and bacterial DNA using a combination of size exclusion-based separation and differential cell lysis prior to DNA analysis. The present invention employs size-based filtration and differential enzymatic treatments combined with an optional oligonucleotide 'pull-down' method for the separation of the DNA sources that are present in an unknown sample into different categories or organismal fractions. More specifically, the present invention is a method of processing a mixture of bacterial cells, plant cells, and cells from the kingdom Animalia prior to sequencing that employs the steps of obtaining a tissue sample containing a plurality of bacterial cells, a plurality of plant cells and a plurality of cells from the kingdom Animalia, forming a mixed solution of bacterial, plant and animal by combining the tissue samples (plant and animal) with a first amount of phosphate-buffered saline in a vessel so that the plurality of bacterial cells, plurality of plant cells and the plurality of animal cells are in suspension. Filtering the mixed plant, animal and bacterial solution a first time using a first wetted filter into a first centrifuge tube to separate a first residue from a first filtrate. Filtering the first filtrate again a second time using a second wetted filter into the same first centrifuge tube to separate a second residue from a second filtrate. Washing the first residue from the first wetted filter with a third amount of phosphate-buffered saline into a first collection tube, washing the second residue from the second wetted filter with a fourth amount of phosphate-buffered saline into the first collection tube. Centrifuging the first wetted filter, the second wetted filter, the first residue, and the second residue in a second centrifuge tube to form a first pellet, and centrifuging the first centrifuge tube to form a second pellet. Forming a first suspension of the first pellet in a first lysis solution, forming a second suspension of the second pellet in a second lysis solution, filtering the first lysed suspension with a third wetted filter to separate a third residue from a third filtrate, and washing the third residue from the third wetted filter into a third collection tube. The first wetted filter may have a pore size of 5 μm. The second wetted filter may have a pore size of 5 μm. The third wetted filter may have a pore size of 5 μm. The first amount of phosphate-buffered saline may comprise 250 μL. The second amount of phosphate-buffered saline may comprise 250 μL. The third amount of phosphate-buffered saline may comprise 250 μL. The first wetted filter and the second wetted filter may each be cut into four equal pieces prior to centrifuging. The first lysis solution may comprise a 2 percent sodium dodecyl sulfate lysis buffer. The second lysis solution may comprise a 2 percent sodium dodecyl sulfate lysis buffer. The method may further comprise the step of incubating the first suspension of the first pellet in the first lysis solution for a first predetermined time period at a first predetermined temperature. The method may further comprise step of incubating the second suspension of the second pellet in the second lysis solution for a second predetermined time period at a second predetermined temperature.

The method of the present invention thus exploits the differences of the cellular size and cellular components of each type of organism to be separated. In particular, the composition and "rigidity" of the cell wall of plant cells, susceptibility of bacterial cells to enzymatic treatments of lyzozyme and overall size difference of bacterial and plant/animal cells allows one portion of a mixed sample to be lysed while retaining the integrity of the remaining organisms. Separation of one phylogenetic component then permits the remaining components to be extracted with minimal contribution from the preceding component. Each type of lysis in the differential method of the present invention involves cellular size filtration separation and a slightly different chemical composition of lysis buffer and incubation that has been modified for the specific targeted organisms. The separation of DNAs from differing contributing phyla in an unknown sample increase interpretability through decreasing complexity in sequencing applications and like-methods.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1A:
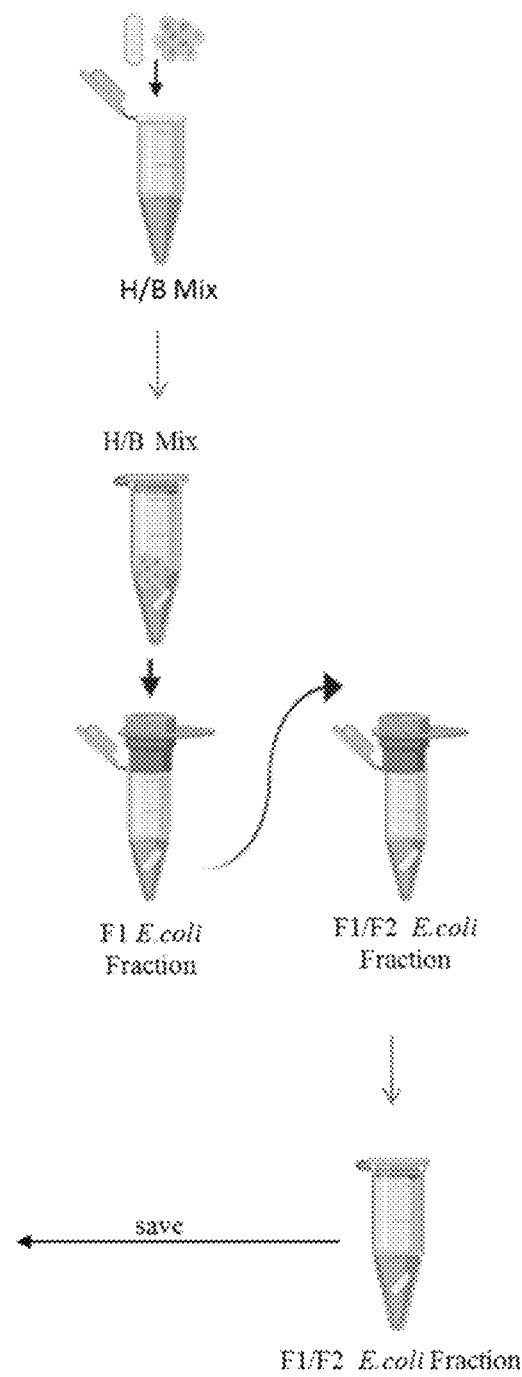
FIGS. 1A through 1D are schematics of the major steps of a method for size exclusion separation of bacterial and human epithelial DNA according to the present invention.
Figure 1B:
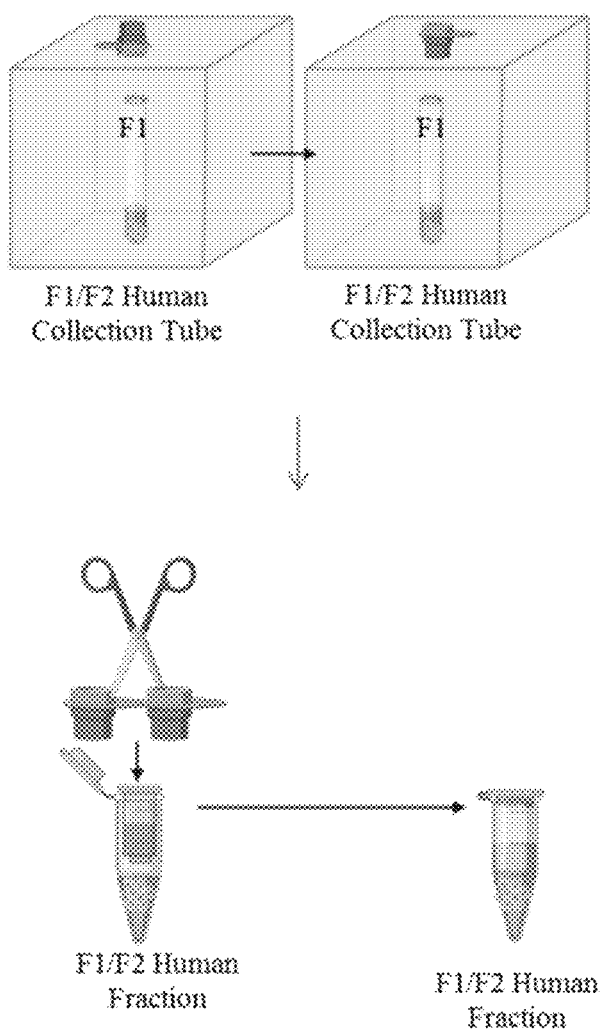
Figure 1C:
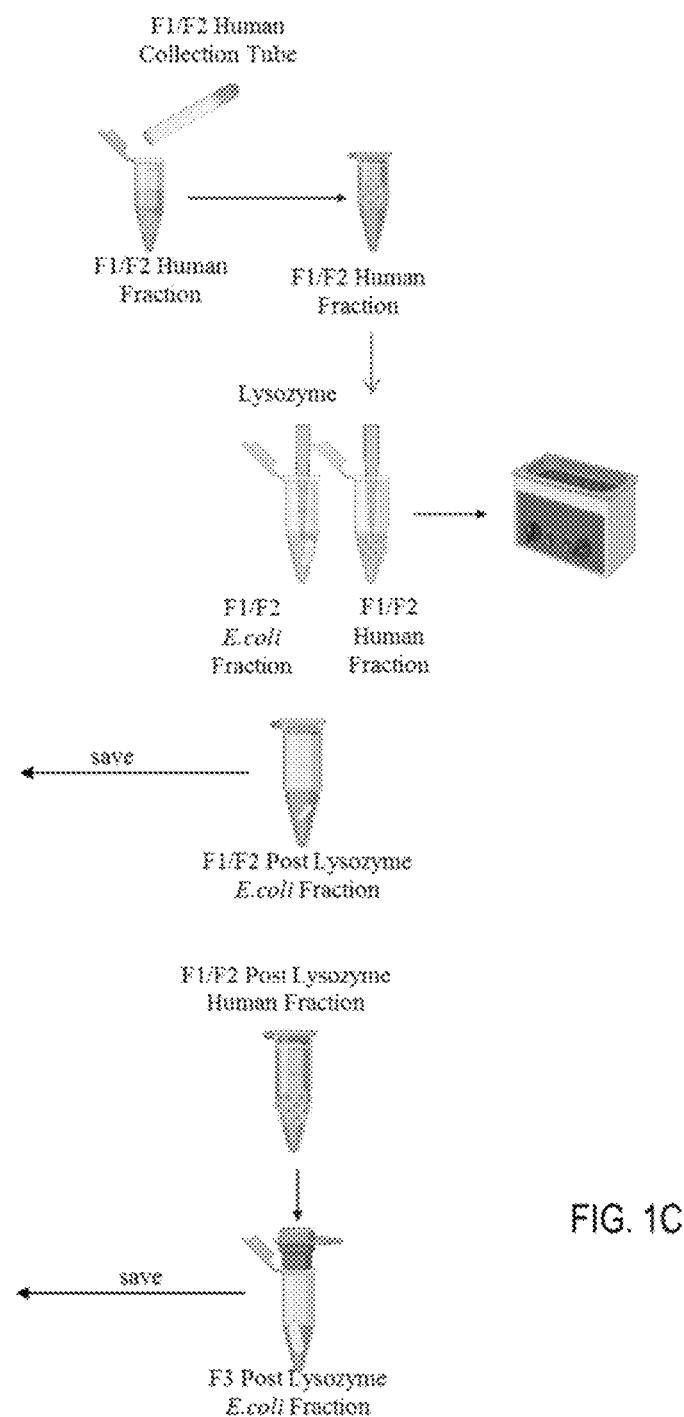
Figure 1D:
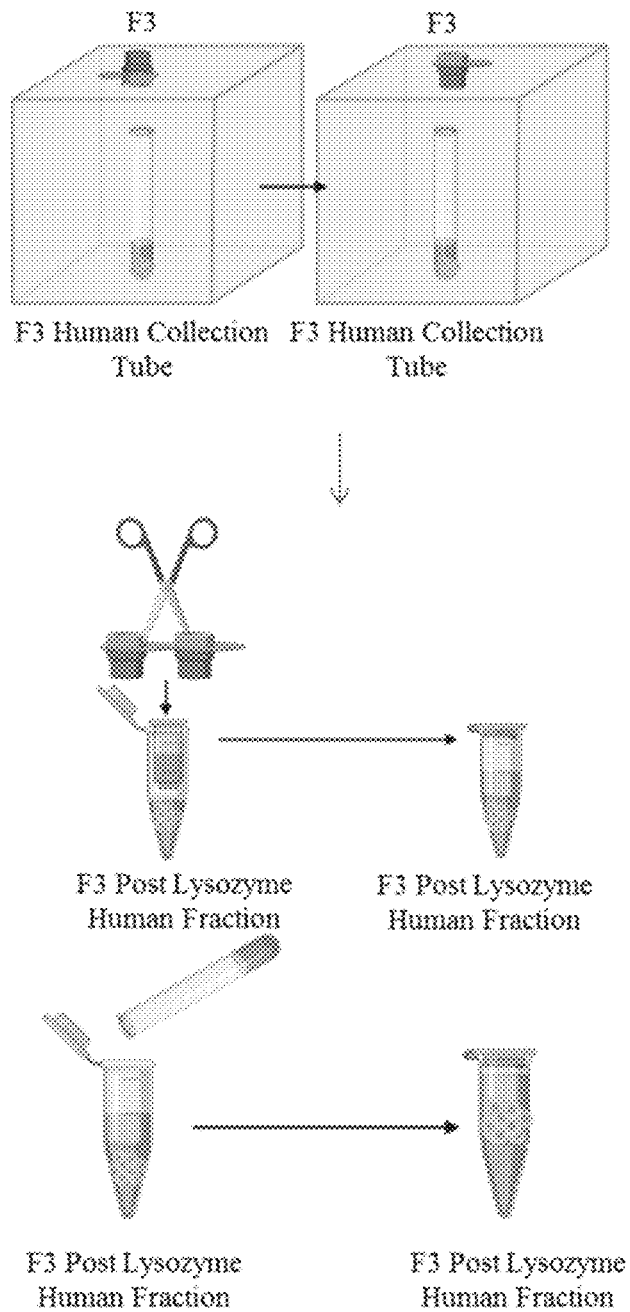

Referring to the figures, wherein like numeral refer to like parts throughout, there is seen in FIGS. 1A through 1D a flowchart of the chief aspects of a method for differentially isolating eukaryotic (cells from the kingdom Animalia) from bacterial DNA according to the present invention. In a first step, an HB Mix is prepared by pipetting 250 µl of PBS into a clean 1.5 ml centrifuge tube labeled "HB Mix." Each individual stock tube containing both E. coli and epithelial cells, is vortexed briefly to re-suspend. Next, 20 µl of each stock is pipetted into the PBS of the HB Mix tube, being careful to only vortex the Human stock gently to not fragment the cells.

In a second step, a filter is pre-wet by cutting a 10 ml syringe at the 3 ml mark with a razor blade and place syringe onto the vacuum manifold. A clean test tube is placed under the vacuum manifold position where the syringe is attached. One Celltrics® 5 µm filter (F1, right side up) is placed into the syringe securely. The vacuum is turned on low to the "R" setting and 250 µl of PBS is pipetted onto the filter slowly to wet the filter.

In a third step, F1 Filtration is performed by turning the vacuum off and placing the wet F1 (right side up) into a clean, 1.5 ml centrifuge tube labeled "F1 E. coli Fraction". Once F1 has no more visible droplets of liquid remaining on top (5 minutes), HB Mix is added and the filter is washed with 250 µl PBS and left to wait for another 5 minutes. This process is repeated with a second wash of 250 µl PBS onto F1, waiting until the filter has no visible liquid remaining on top between each wash (10 minutes) with no force applied by pressure or tapping.

In a fourth step, Filter 2 is placed into the syringe on the vacuum manifold and the third step repeated while the second wash is filtering.

In a fifth step, the vacuum is turned off and the wet filter (F2, right side up) is placed into a clean, 1.5 ml centrifuge tube labeled "F1/F2 E. coli Fraction".

In a sixth step, F1 is carefully lifted out of the F1 E. coli Fraction tube and the remaining liquid pipetted off from the bottom of the tube into the F1 E. coli Fraction.

In a seventh step, parafilmed F1 (upside down) is placed onto the syringe securely.

In an eighth step, F2 Filtration is performed. Once F1 is on the syringe of the manifold, all of "F1 E. coli Fraction" is pipetted onto F2 for second filtration. Once all of the liquid has filtered through (5 minutes), the 250 µl PBS wash is repeated by pipetting the PBS into the F1 E. coli Fraction tube and then onto F2 to make sure that all liquid from F1 E. coli Fraction is added to the F2. This is repeated with a second wash of 250 µl PBS onto F2, waiting until the filter has no visible liquid remaining on top between each wash (10 minutes) with no force applied by pressure or tapping.

In a ninth step, a Vacuum Manifold is used while the second wash is filtering, by turning the vacuum on low "R" setting and carefully pipetting 250 µl of PBS into the upside-down F1, slowly and making sure to cover the entire surface of the filter. This is repeated once the liquid has reached the test tube labeled F1/F2 human collection tube. The vacuum is then turned off and parafilm removed. F1 is turned back right-side up and placed into the syringe. The vacuum is turned on the high "2" setting. F1 is washed with 150 µl PBS, keeping the vacuum on the high setting until all liquid has moved to the F1/F2 human collection tube. The vacuum is turned off and F1 removed. The F1/F2 human collection tube should remain in place for the second collection.

In a tenth step, a clean scalpel is used to remove the filter from F1 and the filter is cut into 4 equal pieces with clean forceps and scissors. The filter pieces are carefully placed into a clean Spin Ease basket in a 1.5 ml centrifuge tube labeled "F1/F2 Human Fraction".

In an eleventh step, F2 is carefully lifted out of the F1/F2 E. coli Fraction tube and the remaining liquid pipetted off from the bottom of the tube into F1-B and the tube is closed.

In a twelfth step, Parafilm F2 (upside down) is placed onto the syringe securely.

In a thirteenth step, steps nine and ten are repeated with F2.

In a fourteenth step, 100 µl of PBS is pipetted onto the filter pieces in the Spin Ease basket, which is vortexed gently and centrifuged briefly. The Spin Ease basket is removed and discarded.

In a fifteenth step, all contents of F1/F2 human collection tube are pipetted into the centrifuge tube labeled "F1/F2 Human Fraction".

In a sixteenth step, both F1/F2 E. coli Fraction and F1/F2 Human Fraction centrifuge tubes are centrifuged for 6 minutes at 10,000×g.

In a seventeenth step, the supernatant is removed until 100 µl is remaining in both tubes, being careful not to disturb the pellet.

In an eighteenth step, the cell pellet is resuspended in 200 1µ2% SDS lysis solution or premade Lysozyme lysis buffer (50 mM Tris (pH 8.0), 5 mM EDTA, 1 mg/ml lysozyme, 50 mM NaCl)

In a nineteenth step, the sample and lysis buffer are allowed to incubate for 30 minutes at 37° C.

In a twentieth step, for the F1/F2 Human Fraction sample only (leave the F1/F2 E. coli Fraction tube in the 37° C. water bath until the $3^{rd}$ filtration is complete), the single 5 µm Celltrics® filter protocol is repeated.

In a twenty-first step, the vacuum is turned on low to the "R" setting and 250 µl of PBS is pipetted onto the filter slowly to wet the filter. The test tube with PBS is discarded.

In a twenty-second step, the vacuum is turned off and the wet filter (right side up) is placed into a clean, 1.5 ml centrifuge tube labeled "F3 Post Lysozyme E. coli Fraction".

In a twenty-third step, the F1/F2 Post Lysozyme Human Fraction tube is vortexed briefly/gently and all 300 µl pipetted onto the wet filter slowly but covering the entire surface of the filter.

In a twenty-fourth step, after 5 minutes, once the filter has no more visible droplets of liquid remaining on top, the filter is washed with 250 µl PBS.

In a twenty-fifth step, after 5 minutes, washing is repeated with a second wash of 250 µl PBS onto the filter, waiting until the filter has no visible liquid remaining on top between each wash (10 minutes) with no force applied by pressure or tapping.

In a twenty-sixth step, the filter is carefully lifted out of the "F3 Post Lysozyme E. coli Fraction" tube and the remaining liquid pipetted off from the bottom of the tube into the same tube.

In a twenty-seventh step, the "F3 Post Lysozyme E. coli Fraction" tube is not discarded and is set aside to save but not extract.

In a twenty-eight step, the filter (upside down) is parafilmed onto the syringe securely. A clean test tube labeled "F3" is placed below the syringe in the manifold filter. The process is repeated once the liquid has reached the test tube labeled F3.

In a twenty-ninth step, the vacuum is turned off and the parafilm removed. The filter is turned back right-side up and placed into the syringe. The vacuum is turned on the high "2" setting.

In a thirtieth step, the filter is washed with 150 µl PBS, keeping the vacuum on the high setting until all liquid has moved to the F3 Human collection tube.

In a thirty-first step, the vacuum is turned off and the filter carefully removed with the scalpel. The filter up is cut into 4 equal pieces with clean forceps and scissors. The filter pieces are placed into a clean Spin Ease Basket in a 1.5 ml centrifuge tube labeled "F3 Post Lysozyme Human Fraction".

In a thirty-second step, 100 µl of PBS is pipetted onto the filter pieces in the Spin Ease basket, which is then vortexed gently and centrifuged briefly. The Spin Ease basket is removed and discarded.

In a thirty-third step, all contents of F3 Human collection tube are pipetted into the centrifuge tube labeled "F3 Post Lysozyme Human Fraction".

In a thirty-fourth step, the F3 Human collection tube is replaced with a clean test tube. The vacuum is turned on the high "2" setting and the syringe washed with ethanol, bleach, and ethanol again.

In a thirty-fifth step, the washing test tube and the syringe are discarded.

With respect to forensic science, the present invention provides for higher information content to be extracted from biological samples, allowing microbial, plant and animal (including human) DNA signatures to be identified and used to determine the source/point of origination, areas where the item has been exposed (geographical) individual donors of the sample. With respect to healthcare and related research, human microbiome characterization is improved by providing the ability to remove the non-target cells and DNAs (human and/or plant) from the bacterial fraction. With respect to metagenomics and environmental DNA analyses, the present invention allows for the deconvolution of complex samples containing multiple organisms, thereby allowing for better characterizations of the individual organismal components.

The development of the three cell-type separation method is the most significant aspect of the present invention. Similar to the previous two-cell type method, the present invention uses size-based filtration and enzymatic treatments. There are features of plant cells that can be exploited to ensure separation. Plant cells are between 10-100 µM in length and have rigid cell walls that protect the cell. The size and rigidity mean they will likely withstand the chemical treatments used for bacterial and mammalian cells without lysing. Therefore, we predict that plant cell separation will be placed at the end of procedure. The bacterial fraction will separate due to the size differences between the prokaryotic and eukaryotic cells and the use of lysozyme. The remaining mixture of both mammalian and plant cells will be treated with a 10% SDS solution, a strong detergent, that helps break open mammalian cells but will likely not be strong enough to lyse the plant cells. Either a size-based filtration or centrifugation may be used to separate the mammalian DNA from the intact plant cells. Plant cells will be lysed using a combination of mechanical lyses such as bead beating or sonication and an enzymatic method using cellulase and SDS.

EXAMPLE

Three species-specific primer sets for *Escherichia coli*, *Homo sapiens*, and *Arabidopsis thaliana* were chosen to represent the three categories of organisms. Each representative was extracted separately, utilizing the portion of the differential lysis and extraction protocol designed for that organism. DNA was quantified using the Nanodrop 2000 and amplified using gradient PCR on the Veriti thermal cycler to determine a collective optimal annealing temperature. For *A. thaliana*, the Maxwell RNA LEV kit was utilized to extract approximately 30 ng/µl of DNA from 0.2 grams of seeds. Stock primers were diluted to 300 nMol working solutions. For H. sapiens, Maxwell DNA LEV kit was utilized to extract approximately 120 ng/µl buccal swab epithelial cell DNA. Stock primers were diluted to 300 nMol and 1.0 µMol working solutions to determine primer molarity for amplification with 10 ng/µl template DNA. For *E. coli*, the Qiagen DNA MiniKit extraction protocol was utilized for gram-negative bacteria: 7.0 ng/µl DNA. A modified protocol was then used to improve concentration (15 ng/µl) with 75% Guanidinium Isothiocyanate (GITC) lysis solution and a 20 mg/ml lysozyme/Buffer AE solution. Stock primers were diluted to 1.0 µMol working solutions.

Agarose Gel Electrophoresis:

Several 4% agarose gels were prepared with 2.0 grams of Molecular Biology Agarose powder (Bio-Rad Certified®), 50.0 mL of 1× Tris-Acetate-EDTA (TAE) buffer, and 6.0 µl Ethidium Bromide (EtBr).

Pre-extraction Cell Count for Animal and Bacterial Samples:

All *H. sapiens* epithelial cells were counted on a Reichert Bright-Line™ hematocytometer with 6.0 µl of sample combined with 6.0 µl Tryphan Blue stain (gibco® 0.4%) for a total volume of 12.0 µl and dilution factor of 2.0. The equation utilized for total number of cells/µl was: (Equation 1). Each stock sample was counted twice in replicate on hematocytometer (the Reichert Bright-Line™) and visualized with a microscope (LEICA CME) at 10× magnification. The total average cell/µl was used as the stock concentration. All *E. coli* samples were counted on the NanoDrop™ 2000 UV/Vis Spectrophotometer (Thermo Scientific) prior to extraction by measuring the optical density at 600 nm (OD600). The following equation was then applied to the OD readings: (Equation 2). Each stock sample was counted twice in replicate and the total average cell/mL was used as the stock concentration. Average bacterial cell count per swab was: 17,109 cells/ml. Average animal epithelial cell count per swab was 65,541 cells/ml Lysis Buffer Preparation The Lysozyme lysis buffer for *E. coli* was prepared with 0.5 mL 1M Tris (Invitrogen UltraPure™, pH 8.0), 0.5ML Grade 500 mM EDTA solution (Calbiochem ULTROL®, pH 8.0), 0.1461 g Sodium Chloride (Sigma Aldrich BioXtra, 99.5%), 0.05 g 20 mg/ml Lysozyme (Alfa Aesar), and 41 mL ddH20. The 10%, 1%, and 2% SDS lysis buffers for *E. coli* and *H. sapiens* were prepared with 0.5 mL 1M Tris (Invitrogen UltraPure™, pH 8.0), 1.0 mL Grade 500 mM EDTA solution (Calbiochem ULTROL®, pH 8.0), 2.922 g Sodium Chloride (Sigma Aldrich BioXtra, 99.5%), 25.0 mL/2.5 mL/5.0 mL Sodium Dodecyl Sulfate 20% Solution (Ambion®), and 23.5 mL/43.5 mL/46 mL ddH20.

Quantitation of Extracted DNA

DNA quantities were obtained using the NanoDrop™ 2000 UV/VIS Spectrophotometer (Thermo Scientific) post-extraction in replicates of 2.0 µl aliquots. Each samples A260, A280, A260/A280, and ng/µl readings were recorded and the average DNA concentration of both replicates was also recorded.

qPCR Set-Up and Analysis

After each sample had been quantitated, a MasterMix of qPCR components was prepared in a 1300 Series A2 biosafety cabinet with the following reagents for a total volume of 15.0 µl per sample: 10.06 µl ddH$_2$O, 1.49 µl FastStart High Fidelity Reaction Buffer with MgCl$_2$ (Roche), 0.29 µl PCR Grade Nucleotide Mix (Roche), 0.11 µl Hot Start DNA Polymerase (OneTaq®), and 0.44 µl 1:75 SYTO9 (Thermo Scientific). The MasterMix was vortexed and centrifuged briefly, followed by the addition of 11.95 µl MasterMix to each of the sample wells of a 384-well PCR microplate (Axygen®). Each well contained 2.0 µl of sample in replicate and 1.05 µl species-specific primer mixture at 300 nM concentration. The plate was sealed tightly with Ultra Clear Pressure Sensitive sealing film (Axygen®) and placed into an Eppendorf centrifuge 5430 briefly before being placed into the LightCycler® 480 II (Roche). The following program was used for each qPCR run for all samples:

Denature—1 cycle:
96° C.—1 minute, ramp rate 4.8° C./s
Phase II—45 cycles
Denature—96° C.-30 seconds, ramp rate 4.8° C./s
Anneal—57° C.-45 seconds, ramp rate 2.5° C./s
Extend—72° C.-1 minute, ramp rate 4.8° C./s
Termination—1 cycle
72° C.—15 minutes, ramp rate 4.8° C./s
HRM-1 cycle
95° C.—1 minute, ramp rate 4.8° C./s
40° C.—1 minute, ramp rate 2.5° C./s
65° C.—1 second, ramp rate 4.8° C./s
95° C.—continuous, ramp rate 0.04° C./s Analysis of the qPCR data was performed via LightCycler® 480 Software (Roche, Version 1.5.0.39) by Abs Quant/Fit Points or Abs Quant/2nd Derivative Max Analysis mode. The sample wells were highlighted and then calculated according to the appropriate analysis mode. The sample names and Cp values were recorded for both replicates and the average Cp value was utilized in the overall analysis of the filtration.

Vacuum Apparatus Filtration

A single 5 µM filter (Celltrics®) was added to a 10 mL syringe that had been cut off at the 3 mL mark and placed onto a vacuum manifold with a plastic test tube for collection inside the manifold. 100 µL Phosphate Buffered Saline (PBS) was added to the top of the filter while the vacuum was on to prime the filter. The filter was removed from the manifold and placed into a 1.5 mL centrifuge tube (Eppendorf) for F1A collection. 200 µl of PBS combined with 20 µl pre-counted *E. coli* cells and 20 µl pre-counted human epithelial cells was pipetted onto the wet filter followed by 2 washes of 250 µl PBS. F1A contents was pipetted onto a new primed 5 µM filter (Celltrics®) for F1B collection in a new centrifuge tube. Both filters were parafilmed onto the vacuum manifold separately with a new collection tube labeled "F2". Both filters were washed with 250 µl PBS twice while upside down and 100 µl PBS when returned to the upright position. Collection tube contents were transferred to a 1.5 mL centrifuge tube (Eppendorf) and all 3 tubes were centrifuged at 10,000×g for 6 minutes. After Lysozyme (Alfa Aesar) lysis of F1B and F2, the F2 tube was then filtered with a single 5 µM filter (Celltrics®) with the same protocol and divided into F2A and F3 tubes.

Post-Filter DNA Extraction

Upon completion of pelleting the cells from the pre-extraction double-filter procedure, supernatant from both F1B and F2 tubes was discarded until 100 µl liquid remained. 200 µl Lysozyme (Alfa Aesar) was added to each tube followed by vortex and 30-minute incubation at 37° C. in a water bath. The F2 tube was then filtered again and divided into F2A and F3 tubes. Both tubes were centrifuged at 10,000×g for 6 minutes and supernatant was removed. Epithelial cells (F3) were re-suspended in a 2% SDS lysis buffer and F2A was set aside. 50 µl 1% SDS was added to F1B and 50 µl 10% SDS was added to F3 followed by a 10 minute incubation at room temperature. 20 µl Pro K was added to both samples before a 10-minute incubation at 56° C., and 200 µl 95% cold ethanol was added before the entire contents were pipetted into a QIamp DSP spin column (Qiagen). The silica column extraction proceeded following Qiagen protocol for buccal swab extraction until 50 µl of DNA was eluted with AE Buffer (Qiagen).

Results

Lysis Buffer Preparation and Protocol Development for Cell Membrane-Based Sample Separation An initial method of separation of a mixed biological sample was proposed based upon the cell membrane components of animal cells that are easily lysed with GITC and would leave bacterial cells with peptidoglycan cell walls intact that would require a harsher lysis with enzymatic digestion via Lysozyme and EDTA. Furthermore, even the harsher lysis of the bacterial cells would allow plant cells to remain intact if the biological sample contained varying types of prokaryotic and eukaryotic DNA that could be separated at the kingdom level into 3 respective categories. GITC was proposed because of its properties that can dually lyse cells and inhibit DNases and RNases, while having the ability to strongly bind DNA to silica particles, ideal for silica column DNA extraction post-separation. Since the bacterial portion of the mixture contains both cell walls and cell membranes, the addition of GITC would weaken but not fully lyse the bacterial cells, after which Lysozyme would be added to the cell pellet once the lysed mammalian DNA supernatant was removed and the single-chain protein would break down the peptidoglycan of the remaining cell walls.

Figure 2:
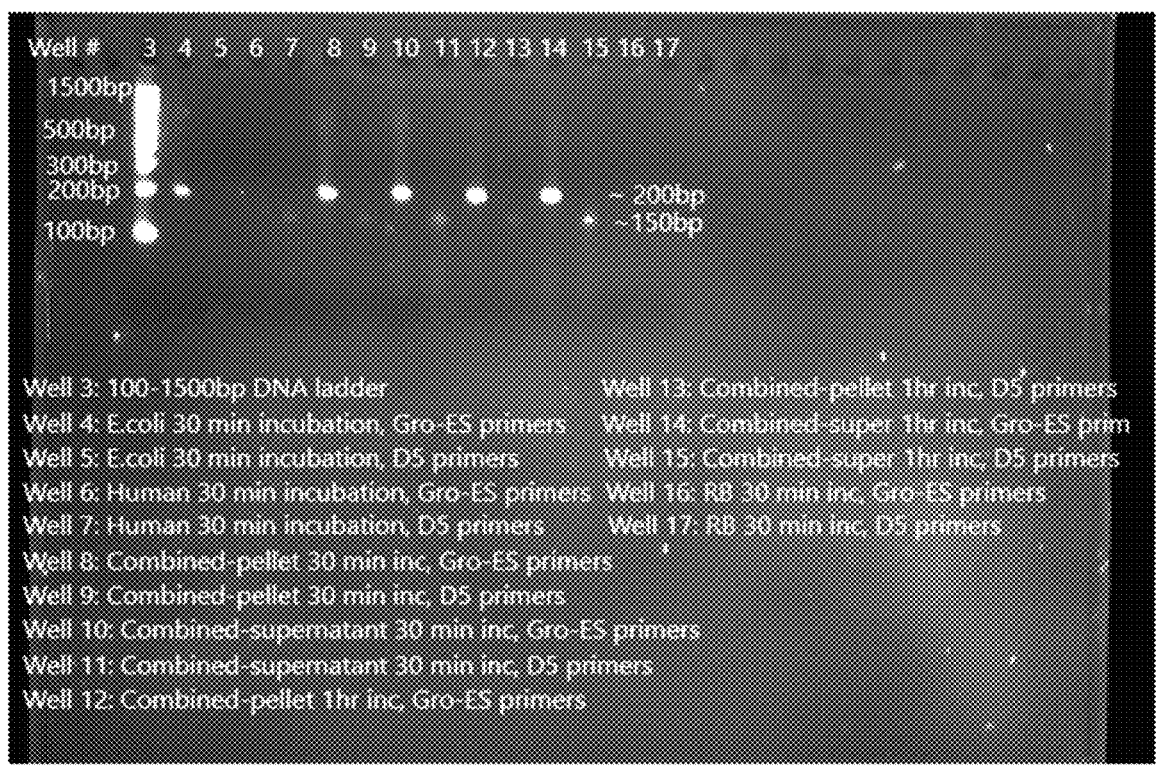
FIG. 2 is an image showing results of a size filtration and enzymatic treatment followed by Qiagen-based isolation with added wash step and varied incubation times.
Figure 3:
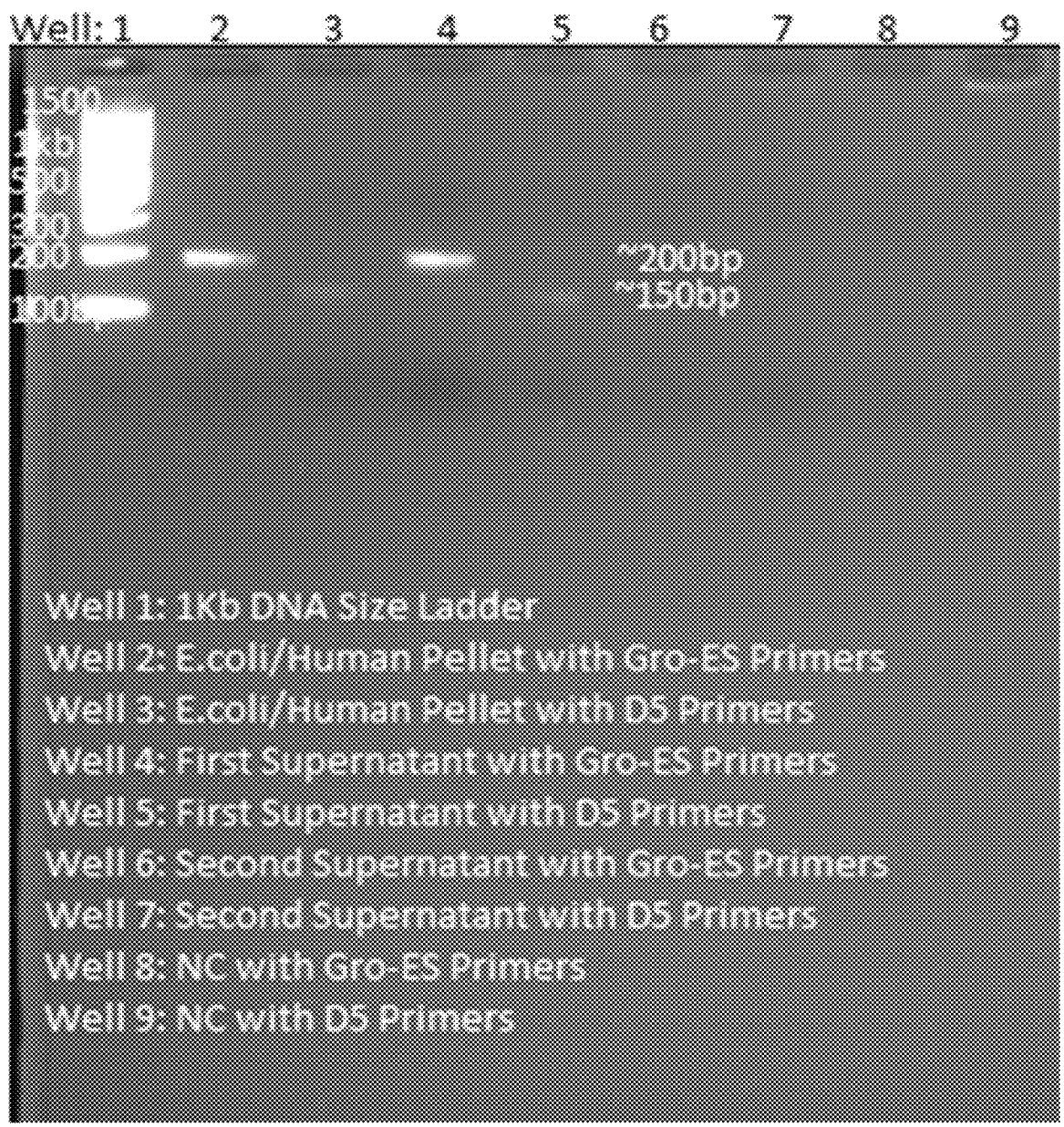
FIG. 3 is an image showing differential extraction using a Qiagen system to lyse human cells first.

A strong GITC lysis solution (5M) added to the mixed *E. coli* and *H. sapien* sample followed by the addition of Proteinase K and SDS lysis buffer. The supernatant was then added to a QIamp spin column and the cell pellet was resuspended in the GITC and 20 mg/ml Lysozyme solution followed by incubation for 1 hour at 37° C. to ensure bacterial lysis and similarly extracted with QIamp spin column. This protocol resulted in extraction of the bacterial cells in both the bacterial and animal portions of the differential extraction (Supplemental FIG. 2). It was determined that the GITC lysis buffer could be used to lyse the bacterial cell portion if needed. The lysis buffer was changed to a 1mg/ml Lysozyme, 50 mM Tris, 50 mM NaCl and 5 mM EDTA solution. Adjustments to the protocol includes Lysozyme wash step after re-suspension of the epithelial cell pellet in 2% and 10% SDS and varying the centrifugation speeds, the Pro K incubation times, and Lysozyme incubation temperatures. All variations resulted in bacterial and epithelial DNA observed in the cell pellet and the $1^{st}$ supernatant prior to the lysozyme wash, as seen in FIG. 1.

FIG. 1 depicts the presence of *E. coli* DNA shown at approximately 200 bp in all combined cell pellets and supernatants (Wells 8, 10, 12, 14) and human epithelial cell DNA shown at approximately 150 bp in all combined cell pellets and supernatants (Wells 9, 11, 13, 15).

The epithelial cell lysis buffer was amended in the protocol to a 2% SDS/10 mM Tris/10 mM EDTA/1M NaCl buffer with varied incubation times. The ProK incubation times were also varied in addition to a gentler centrifugation speed to pellet only the targeted cells prior to separation of supernatant and cell pellet. Once again, results showed presence of both types of DNA in the cell pellet. The SDS percentage was then varied from 0.5%, 1%, and 2% and tested on both types of cells separately. The results from the SDS percentage variation proved that only the 1% SDS lysis buffer was sufficient to lyse the bacterial cells while leaving the epithelial cells intact (Quant data: bacteria 1% SDS-51 ng/µl. Human 1% SDS-7 ng/µl).

The initial proposed order of the differential extraction was reversed to lyse the bacterial cells first with 1% SDS and 1 mg/ml Lysozyme buffer, followed by centrifugation at 10,000×g for 1 minute and separation of the cell pellet at supernatant. 200 µl of the 2% SDS lysis buffer and 50 µl of 10% SDS lysis buffer was then added to the cell pellet which should have contained intact epithelial cells and both portions were simultaneously extracted. However, the results of the reversed bacterial and epithelial separation order still resulted in dual DNA presence in both the cell pellet and the supernatant, as seen in FIG. 1.

The bands at approximately 200 bp represent the *E. coli* DNA presence, observed in both the cell pellet and the $1^{st}$ supernatant. The bands at approximately 150 bp represent the human epithelial cell DNA, observed again in both the cell pellet and the $1^{st}$ supernatant.

10 µM Filtration Method

Given the problematic nature of separating the cellular mixture with differential lysis and centrifugation alone, the addition of a size exclusion filtration was proposed via a 10 µM Celltrics® filter after the Lysozyme incubation at 37° C. for 10 minutes to separate the lysed bacterial cells from the intact epithelial cells. Typical bacterial cell sizes range from 0.5-5.0 µM in length, while most mammalian cells range from 10-100 µM in diameter; therefore, the proposed use of a 10 µM filter would successfully separate both lysed and intact *E. coli* cells from the epithelial cells. In this initial filtration protocol, the use of a single 10 µM filter was proposed to allow the bacterial DNA and cells to flow through the filter and the subsequent capture of the epithelial cells by turning the filter upside down and washing with PBS into a separate tube to collect the epithelial cells.

Figure 4:
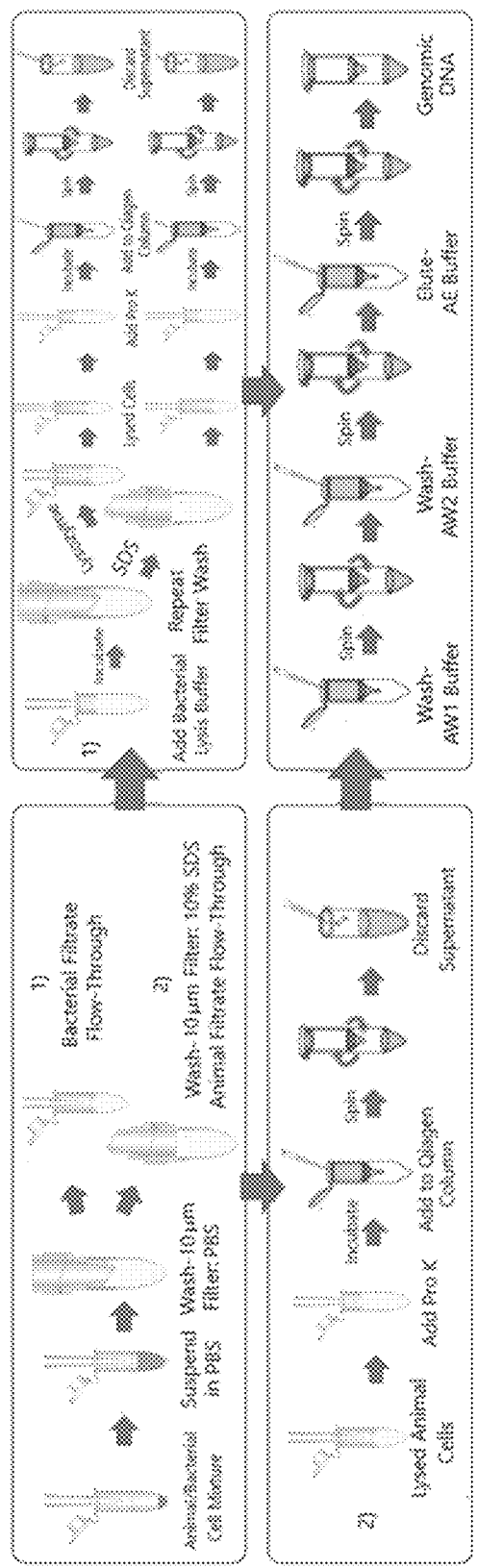
FIG. 4 is a schematic showing a work-flow illustration of the differential extraction protocol development that focuses on separation of bacterial from cells from the kingdom Animalia according to the present invention.
Figure 5:
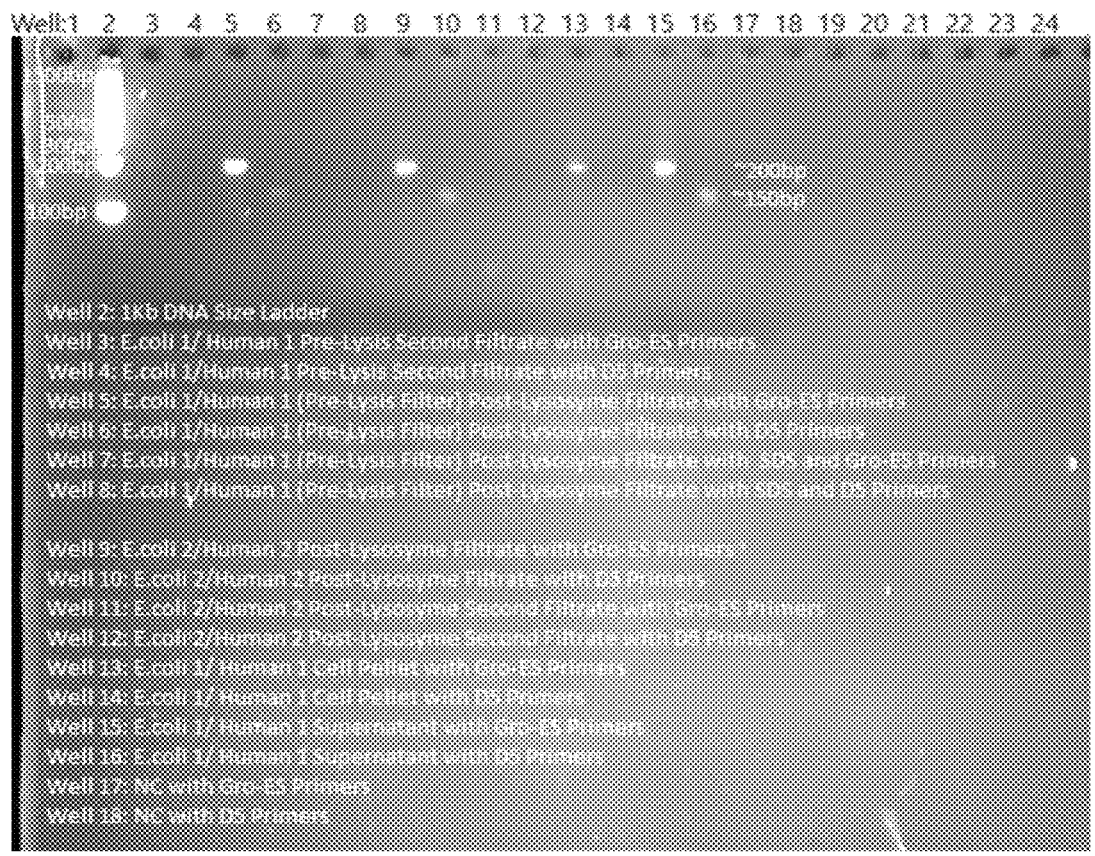
FIG. 5 is an image showing a comparison of size filtration and enzymatic separation at different time points and steps during the course of the differential extractions.

The filter was removed via scalpel and cut into 4 equal sections with forceps and scissors, placed into a Spin Ease basket in a 1.5 ml centrifuge tube and vortexed to remove any epithelial cells that were not collected during the wash steps. Initial results showed that *E. coli* cells were successfully filtered through, but it was determined that most—if not all of the epithelial cells were also filtered through with the *E. coli* despite the 10 µM size of the filter and theoretical knowledge of epithelial cell size, as seen in FIG. 4. FIG. 4 shows the previous cell pellet method of differential extraction with observed *E. coli* DNA in both the cell pellet and supernatant (Wells 13 & 15) and human epithelial cell DNA in the supernatant (Well 16). We compared these results with a 10 µM filter applied prior to any lysis and did not observe any human epithelial DNA in the expected human portion (Well 4). The post-lysozyme filter showed human epithelial cell DNA in the expected bacterial portion (Wells 6 & 10) and *E. coli* DNA present in in expected bacterial portion (Wells 5 & 9). No DNA observed in the $2^{nd}$ filtrate after the post-Lysozyme filter with the addition of SDS (Wells 7, 8, 11, & 12).

10 µM and 5 µM Celltrics® Filtration Size Comparison

Despite known size differences between the species and the theoretical inability of the epithelial cells to get through the 10 µM filter, we proceeded with a 5 µM and 10 µM Celltrics® double filter comparison with bacterial and epithelial cells separately as well as mixed together prior to any lysis steps to determine the best separation yield via size exclusion filtration. Each bacterial and epithelial cell stock was counted prior to filtration and after filtration with OD600 readings and hemacytometer. The first filtration tube of the double filter was termed "F1A", whose contents were then added to a second clean filter and was termed "F1B". The 10 µm Human counts showed that human cells were flowing through the right side up filter (F1A) as well as getting stuck in Filter A (Table 1). None of the human cells were separated from *E. coli* with the 10 µm Filters.

TABLE 1

Human/Epithelial Cells 10 μm Filter Counts.

| Sample:<br>Human/Epithelial<br>10 μm Filter | # Cells per<br>16-Square | Average<br>Number of cells<br>per square | Cells per μl<br>(Avg × 10 × 2) | Total Expected<br>of Human Stock<br>(cells/μl) with<br>26x Dilution |
| --- | --- | --- | --- | --- |
| Human 4 F1A | 4, 0, 1, 1 | 6/4 = 1.5 | 30 | 0 |
| Human 4 F2A | 1, 0, 0, 1 | 2/4 = 0.5 | 10 | 35 |
| Human 4 Filter A | 3, 1, 1, 0 | 5/4 = 1.25 | 25 | 0 |
| Human 5 F1A | 0, 0, 0, 1 | 1/4 = 0.25 | 5 | 0 |
| Human 5 F2A | 0, 0, 1, 1 | 2/4 = 0.5 | 10 | 35 |
| Human 5 Filter A | 0, 0, 0, 0 | 0/4 = 0 | 0 | 0 |
| Human 6 F1A | 2, 2, 0, 0 | 4/4 = 1.0 | 20 | 0 |
| Human 6 F2A | 1, 2, 0, 0 | 3/4 = 0.75 | 15 | 35 |
| Human 6 Filter A | 3, 0, 1, 1 | 5/4 = 1.25 | 25 | 0 |

From stock *E. coli* counts, found prior to filtration, it was calculated that the expected number of cells was 2.60×10^7 cell/mL. After using the NanoDrop 2000™ with the A600 reading, all the *E. coli* from the 10 μM Filter was observed in F1A. No cells were found in any of the other samples. During the 5 μM filtration, it was found that the filter needed to be primed with PBS prior to any filtration in order for the cell suspension to flow through without force. A vacuum manifold was utilized to both prime the filter and when the filter was upside down as an attempt to increase epithelial cell collection in F2A/F2B.

The epithelial cell counts for the 5 μM filter showed that we were able to recover most of the cells in the F2 portion and only a fraction of the cells were still able to get through the filter (Table 2).

TABLE 2

Epithelial Cell 5 μM Celltrics ® Filter Counts

| Sample:<br>Human Epithelial<br>5 μm Filter | # Cells per<br>16-Square | Average<br>Number of cells<br>per square | Cells per μl<br>(Avg × 10 × 2) | Total Expected<br>of Human Stock<br>(cells/μl) with<br>26x Dilution |
| --- | --- | --- | --- | --- |
| Human 1 F1A-vacuum 4 | 1, 1, 1, 0 | 3/4 = 0.75 | 15 | 0 |
| Human 1 F2A | 2, 0, 0, 1 | 3/4 = 0.75 | 15 | 35 |
| Human 1 Filter A | 2, 1, 1, 0 | 4/4 = 1.0 | 20 | 0 |
| Human 2 F1A-vacuum 2 | 1, 1, 1, 1 | 4/4 = 1.0 | 20 | 0 |
| Human 2 F2A | 0, 0, 0, 1 | 1/4 = 0.25 | 5 | 35 |
| Human 2 Filter A | 3, 0, 0, 2 | 5/4 = 1.25 | 25 | 0 |
| Human 3 F1A-no vacuum | 0, 0, 0, 1 | 1/4 = 0.25 | 5 | 0 |
| Human 3 F2A | 0, 1, 1, 2 | 4/4 = 1.0 | 20 | 35 |
| Human 3 Filter A | 0, 0, 0, 0 | 0/4 = 0 | 0 | 0 |

From stock *E. coli* counts, found prior to filtration, it was calculated that the expected number of cells was 2.57×10^7 cell/mL. The *E. coli* 5 μM filter counts depicted the cells were mostly present in F1A with small amounts present in F2A and Filter A (Supplementary Table 2). This corresponded to the 10 μM *E. coli* filter counts with the exception of a small residual amount in the F2 portion.

During the combined sample 5 μM double filtration of both epithelial cells and *E. coli* cells, the same protocol was applied as the individual samples. It was calculated that the expected number of epithelial cells was 34 for C2 and C3, and 20 for C6. It was observed that most cells in either the F2 portion or on the filters, while no epithelial cells were observed in the F1B *E. coli* portion (Table 3). The *E. coli* counts for the combined protocol were calculated to expect 3.0×10^7 cell/mL and it was observed most in the F1B portion with residual amounts in the F2 epithial cell portion, which were the same results obtained from the previous 5 μM study with the bacterial cells separately (Supplementary Table 3).

TABLE 3

Combined Sample-Human cell count 5 μM CellTrics ® Filter.

| Sample:<br>Combined-CellTrics ® | # Cells per<br>16-Square | Average<br>Number of cells<br>per square | Cells per μl<br>(Avg × 10 × 2) | Total Expected<br>of Human Stock<br>(cells/μl) with<br>26x Dilution |
| --- | --- | --- | --- | --- |
| C2 F1B | 0, 0, 0, 0 | 0/4 = 0 | 0 | 0 |
| C2 F2A | 1, 0, 1, 0 | 2/4 = 0.5 | 10 | 34 |
| C2 F2B | 0, 0, 0, 0 | 0/4 = 0 | 0 | 0 |
| C2 Filter A | 0, 2, 0, 1 | 3/4 = 0.75 | 15 | 0 |
| C2 Filter B | 1, 0, 0, 0 | 1/4 = 0.25 | 5 | 0 |
| C3 F1B | 0, 0, 0, 0 | 0/4 = 0 | 0 | 0 |

TABLE 3-continued

Combined Sample-Human cell count 5 μM CellTrics ® Filter.

| Sample: Combined-CellTrics ® | # Cells per 16-Square | Average Number of cells per square | Cells per μl (Avg × 10 × 2) | Total Expected of Human Stock (cells/μl) with 26x Dilution |
|---|---|---|---|---|
| C3 F2A | 1, 0, 2, 1 | 4/4 = 1 | 20 | 34 |
| C3 F2B | 0, 0, 0, 0 | 0/4 = 0 | 0 | 0 |
| C3 Filter A | 0, 0, 0, 0 | 0/4 = 0 | 0 | 0 |
| C3 Filter B | 0, 0, 0, 0 | 0/4 = 0 | 0 | 0 |
| C6 F1B | 0, 0, 0, 0 | 0/4 = 0 | 0 | 0 |
| C6 F2A | 0, 0, 0, 0 | 0/4 = 0 | 0 | 20 |
| C6 F1B | 0, 0, 0, 0 | 0/4 = 0 | 0 | 0 |
| C6 Filter A | 0, 1, 0, 0 | 1/4 = 0.25 | 5 | 0 |
| C6 Filter B | 0, 0, 0, 0 | 0/4 = 0 | 0 | 0 |

Combined 5 μM Celltrics® Double Filtration and Extraction Method

Upon completion of determining the best method for filtration utilizing the 5 μfilters, both cell portions were pelleted for 6 minutes at 10,000×g via centrifugation. The epithelial cells were re-suspended in a 2% SDS lysis buffer and the bacterial cells were re-suspended in a 1 mg/ml Lysozyme lysis buffer based on previous lysis buffer results prior to the filter study. Both samples were incubated at 37° C. for 30 minutes, followed by the addition of 50 μl 10% SDS to ensure proper cellular lysis and a room temperature incubation for 10 minutes. 20 μl Pro K was added to both samples before a 10-minute incubation at 56° C., and 200 μl 95% cold ethanol was added before the entire contents were pipetted into a QIamp DSP spin column. The silica column extraction proceeded until 50 μl of eluted DNA was quantitated via NanoDrop2000 and samples were added to either a 4% agarose gel or 384-well Roche LightCycler® qPCR plate and amplified in replicate with both D-5 human primers and Gro-ES *E. coli* primers. This step was performed to determine the accuracy of the preliminary filter study counts and the exact amount of expected and residual DNA from both samples.

Figure 6A:
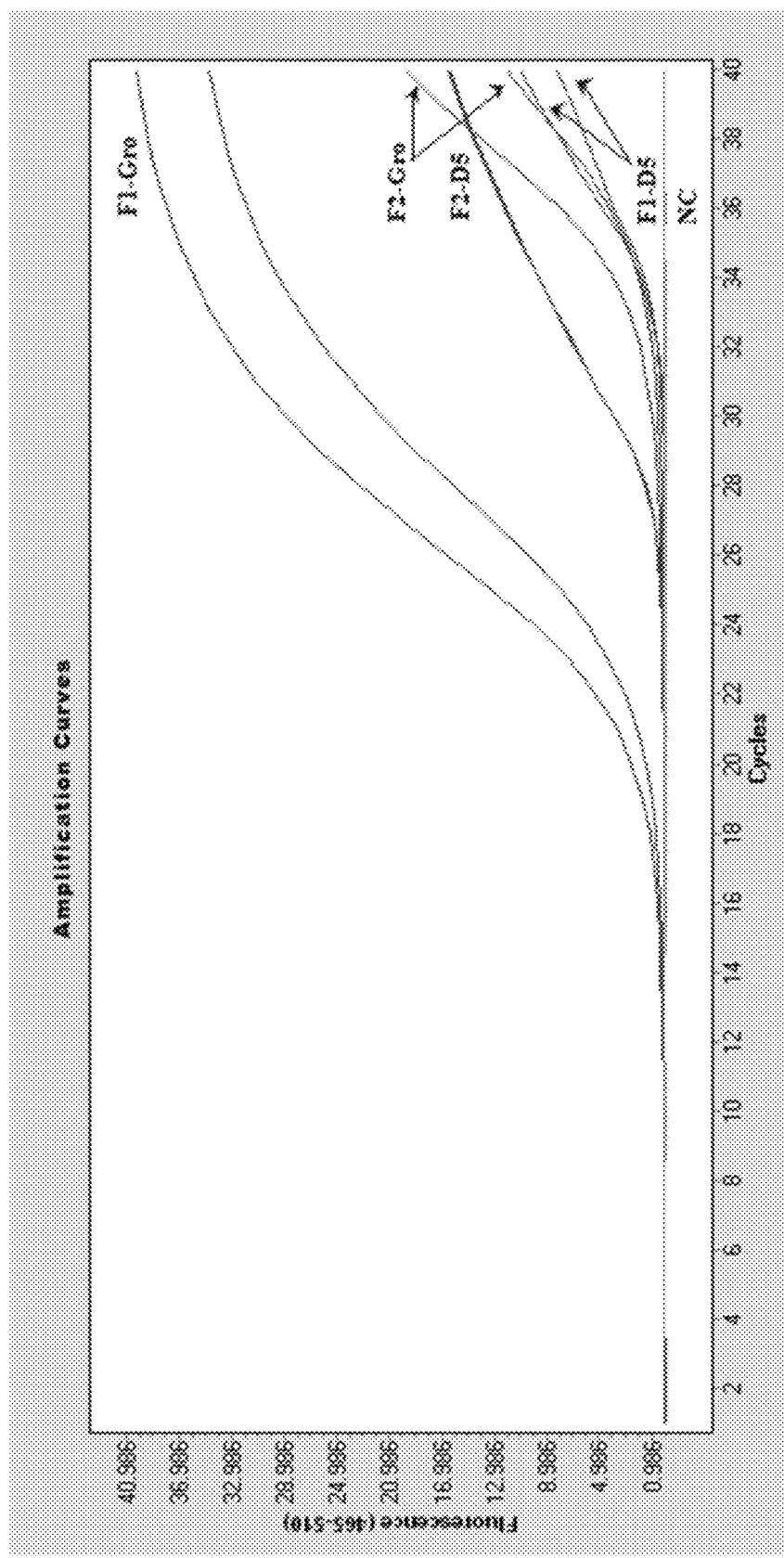
FIGS. 6A through 6C are a series of graphs showing a qPCR Analysis of a 5 µM double filter prior to DNA extraction.
Figure 6B:
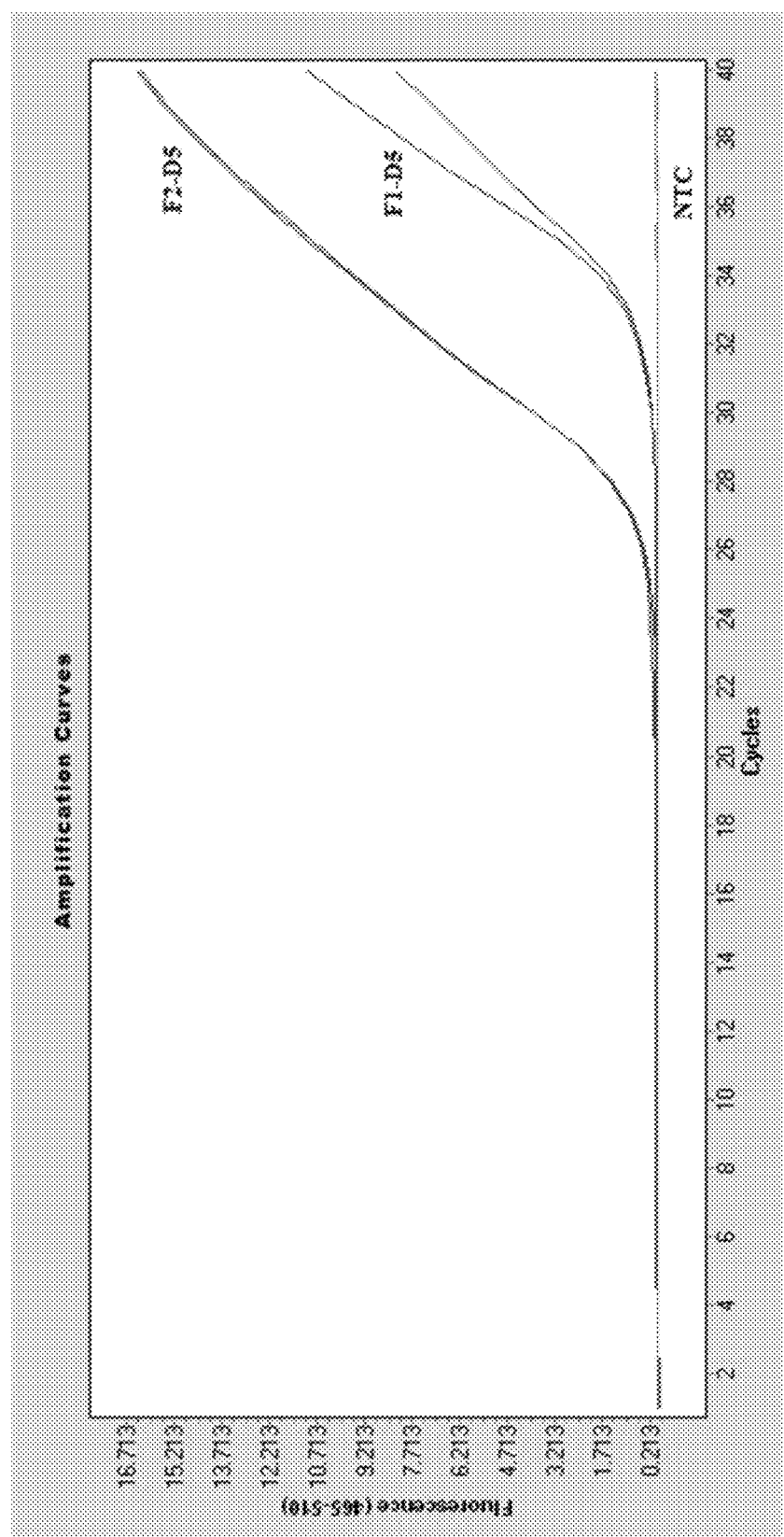
Figure 6C:
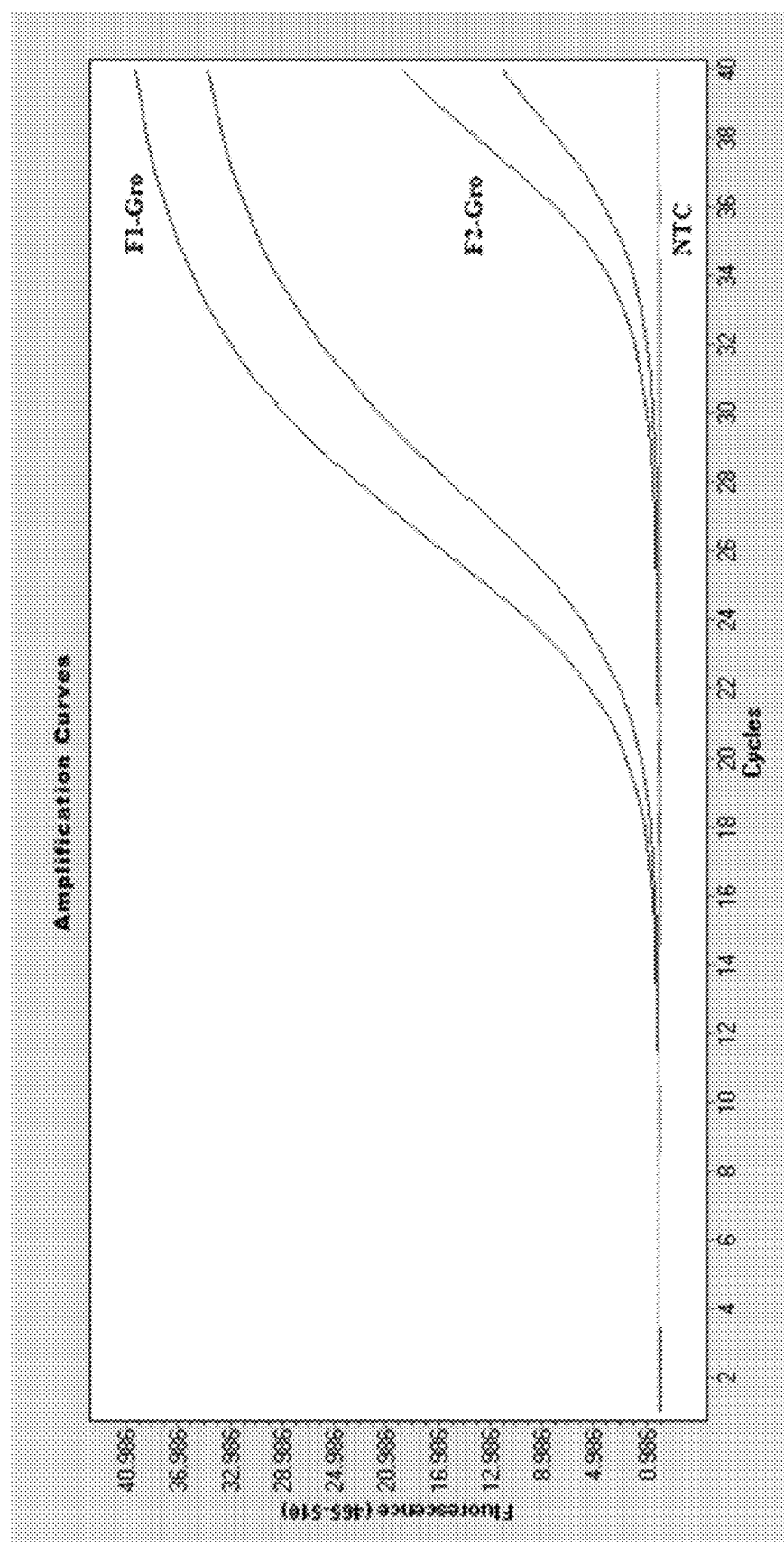

The initial extraction with traditional PCR and agarose gel electrophoresis resulted in loss of human epithelial cell DNA. This led to an amendment of the double-filter protocol to only include 2 washes of 250 μl PBS (per filter) when collecting the "F2" portion with the vacuum manifold while the filter was upside down and 1 wash of 150 μl PBS when the filter was turned right-side up on the manifold. All "F2" washes were collected in the same tube in the manifold and pipetted into a singular 1.5 ml centrifuge tube to minimize cell loss. Both filters were cut up and added to the same Spin Ease basket with 100 μl PBS, vortexed, and centrifuged before the "F2" collection tube contents was added to that centrifuge tube. This allowed all "F2" contents to be in a singular tube before the "F1" and "F2" tubes were centrifuged at 10,000×g for 6 minutes. The first qPCR data from the updated protocol showed decent separation of both types of DNA with some residual DNA in both the F1 and F2 portions, as seen in FIG. 6. This was inconsistent with the quantitation data for the *E. coli* separation from the filter study. However, we had observed successful *E. coli* separation in the previous 10 μM filter when the filter was applied post-lysozyme incubation.

Analysis of the amended double-filter protocol showed the largest amount of observed DNA from recovered *E. coli* DNA in F1B (A&C), followed by recovered human epithelial cell DNA in F2 (A&B), with a small amount of residual *E. coli* DNA in F2 (A&C) and residual epithelial cell DNA in F1B (A&B). The amount of residual DNA in both samples corresponds to the amount of recovered DNA with bacterial showing higher RFU than human (A).

The double-filter protocol with PBS washes remained the same, and both the F1 and F2 portions were re-suspended in 200 μl 1 mg/ml Lysozyme lysis buffer and incubated at 37° C. for 30 minutes as opposed to the F2 portion being re-suspended in 2% SDS. Once the lysozyme incubation was complete, the F2 portion was filtered a 3rd time over a single 5 μM filter with PBS washes in the same amounts as the pre-lysis filtration. The "F1" of this filtration (F2A) was saved but not extracted, and the "F2" portion (now F3) was pelleted and re-suspended in 2% SDS lysis buffer. Once re-suspended in the appropriate lysis buffers, both samples were incubated for 10 minutes at room temperature with an additional 50 μl of 10% SDS to ensure cellular lyses, as previous qPCR and gel electrophoresis data showed a low concentration of epithelial cell DNA compared to the stock concentrations. The samples were then incubated for 10 minutes at 56° C. with 20 μl Pro K and added to QIamp DSP silica columns for extraction. The qPCR data showed a better recovery of epithelial cells in the F3 portion, but also showed residual epithelial DNA in the F1 portion.

It was determined that the previous SDS percentage extraction comparison showed 1% SDS lysis buffer was a sufficient percentage to lyse the bacterial cells and not the epithelial cells. The protocol was amended to add 50 μl of 1% SDS to the F1 portion after filtration and 50 μl of 10% SDS to the F3 portion. The changes of the SDS percentages and the addition of the 3rd port-lysozyme filter of the F2 portion resulted in successful separation of bacterial and epithelial cell DNA with little to no residual DNA in either portion, as seen in FIG. 7.

Figure 7A:
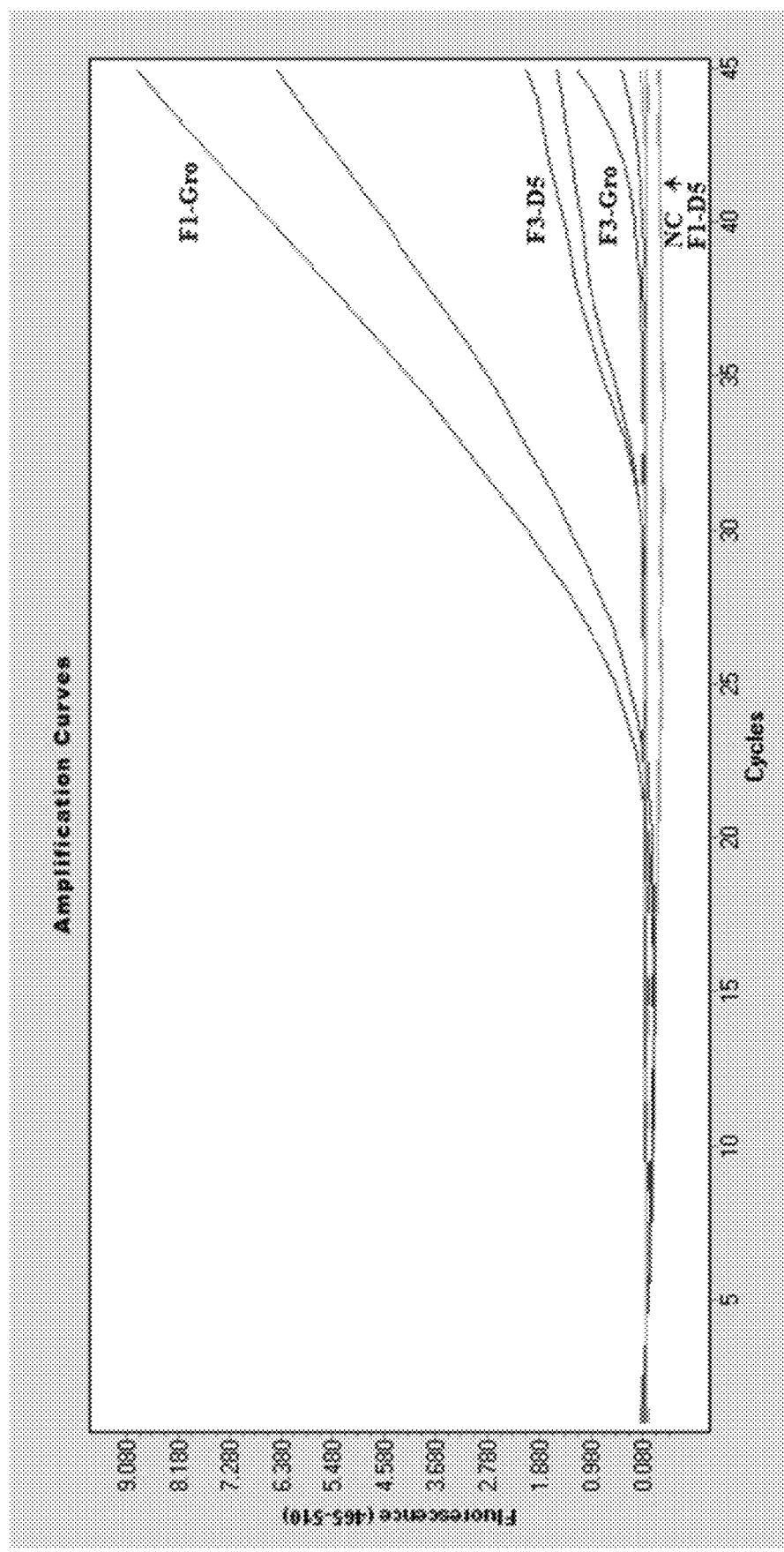
FIGS. 7A through 7C are a series of graphs showing qPCR analysis of a 5 µM double filter prior to DNA extraction with $3^{rd}$ filter post-lysozyme incubation.
Figure 7B:
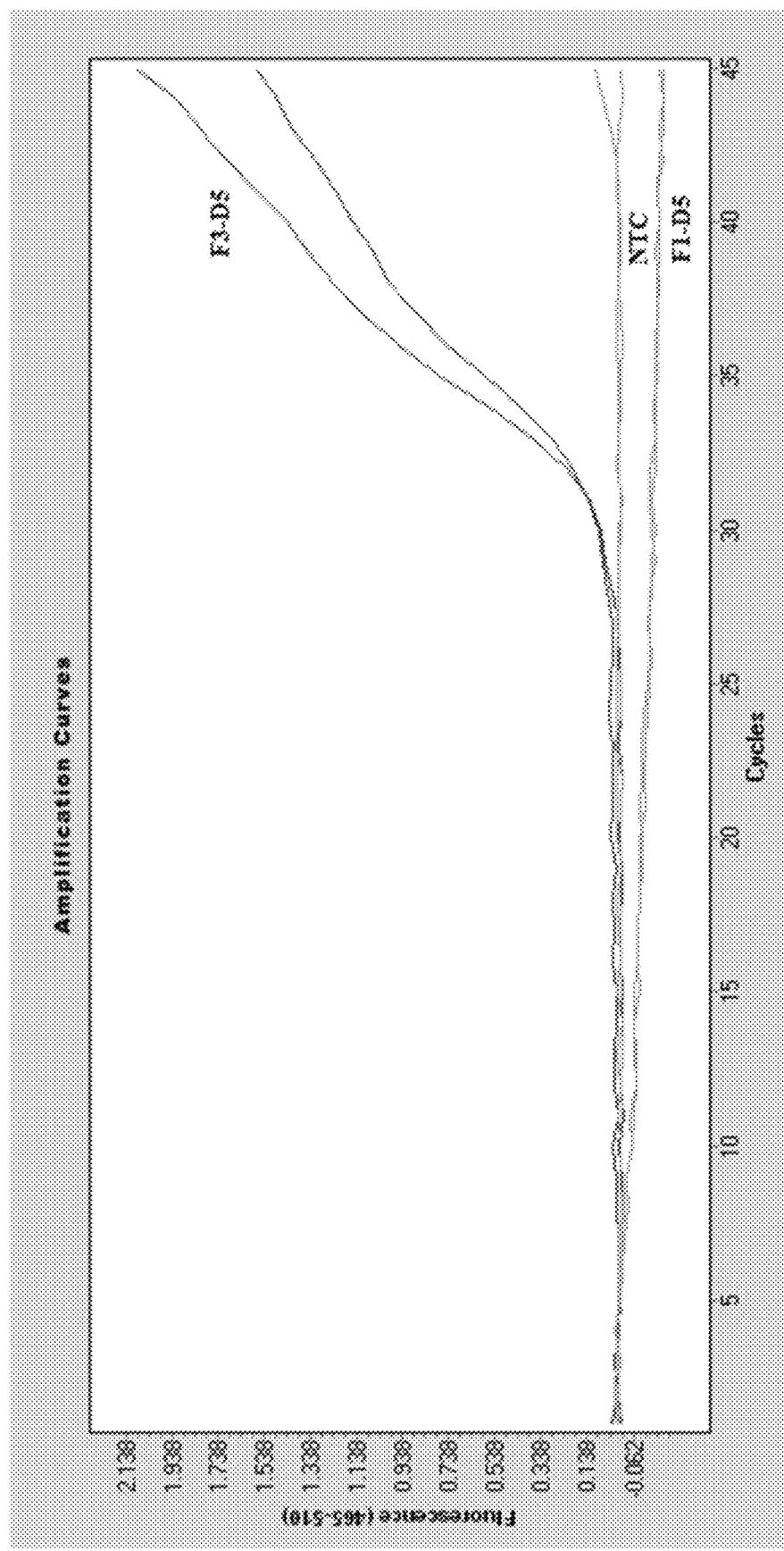
Figure 7C:
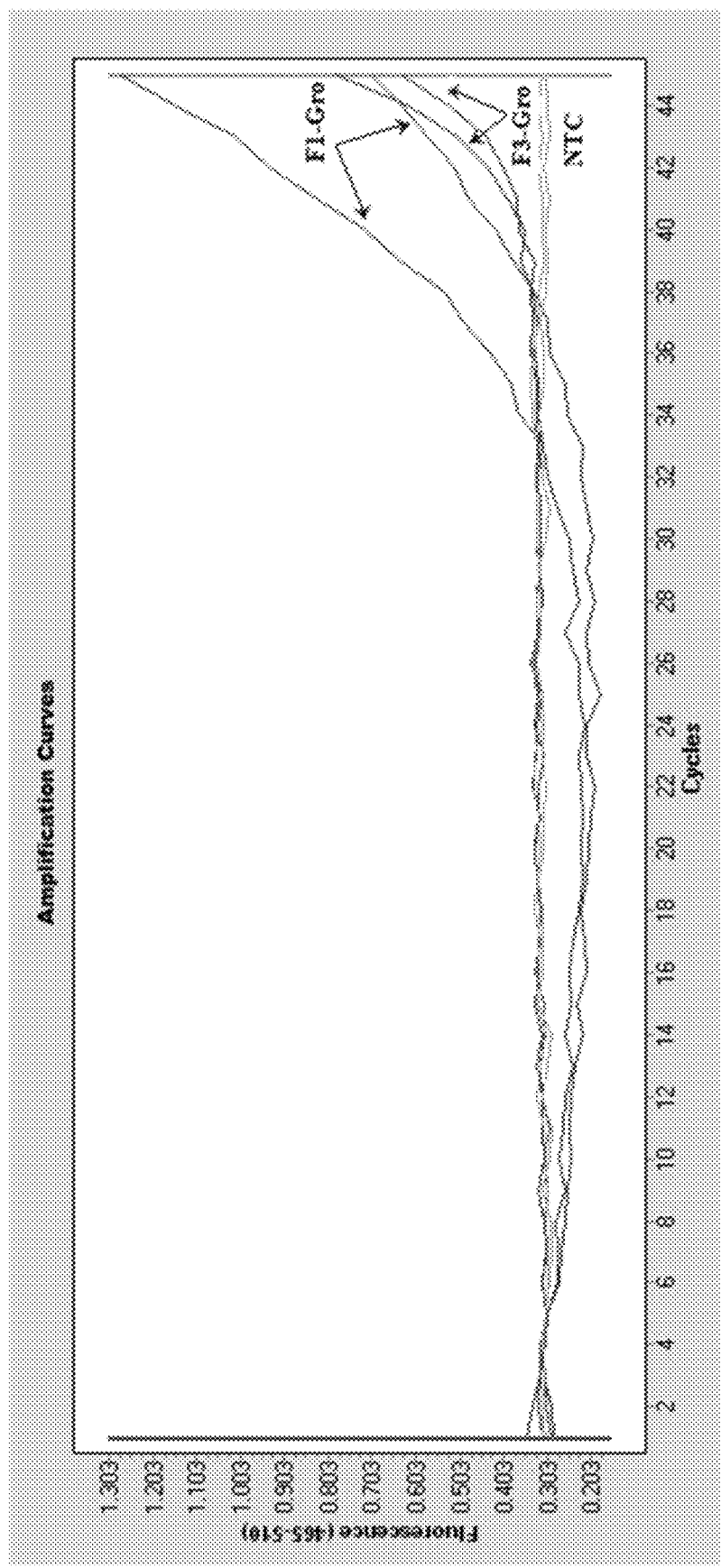

Analysis of the added $3^{rd}$ filter on the F2→F3 portion resulted in the highest observed DNA recovered from *E. coli* in F1 (FIGS. 7A and 7C), followed by recovered human epithelial cell DNA in F3 (FIGS. 7A and 7B). The residual DNA in both samples was extremely low compared to the method without the $3^{rd}$ filter.

Figure 8A:
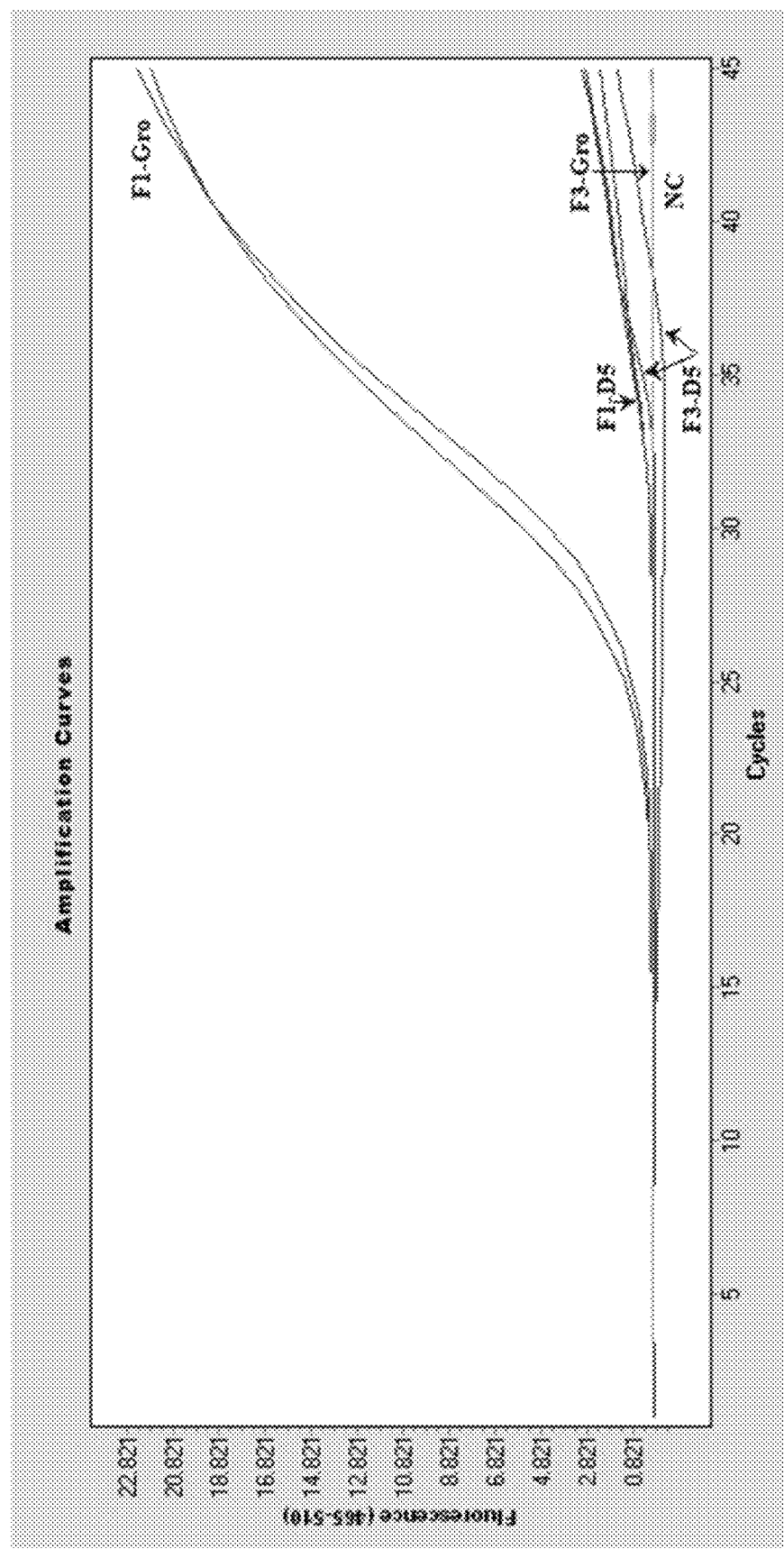
FIGS. 8A through 8C are a series of graphs showing qPCR analysis of a 5 µM double filter prior to DNA extraction with $3^{rd}$ filter post-lysozyme incubation replication.
Figure 8B:
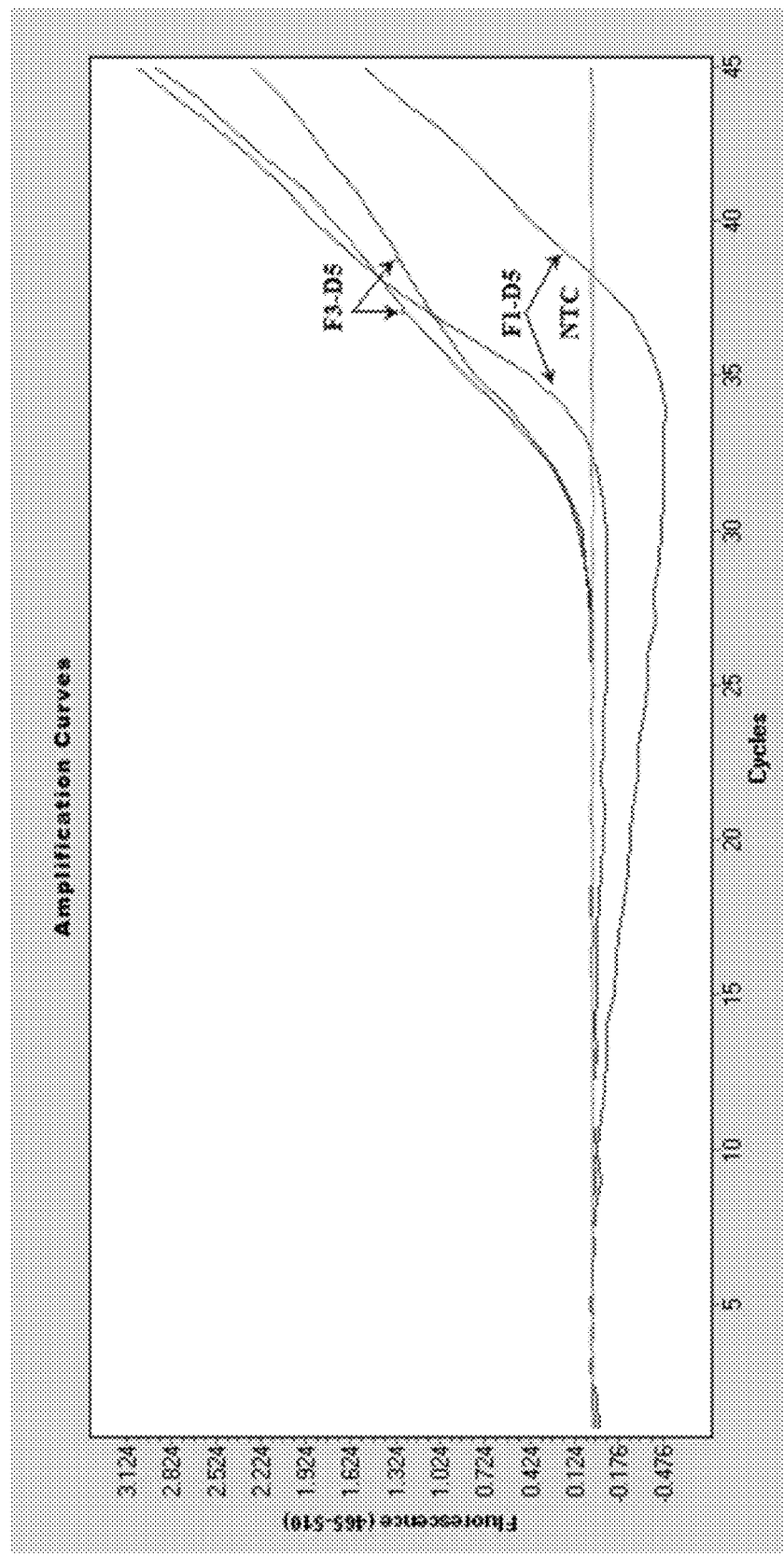
Figure 8C:
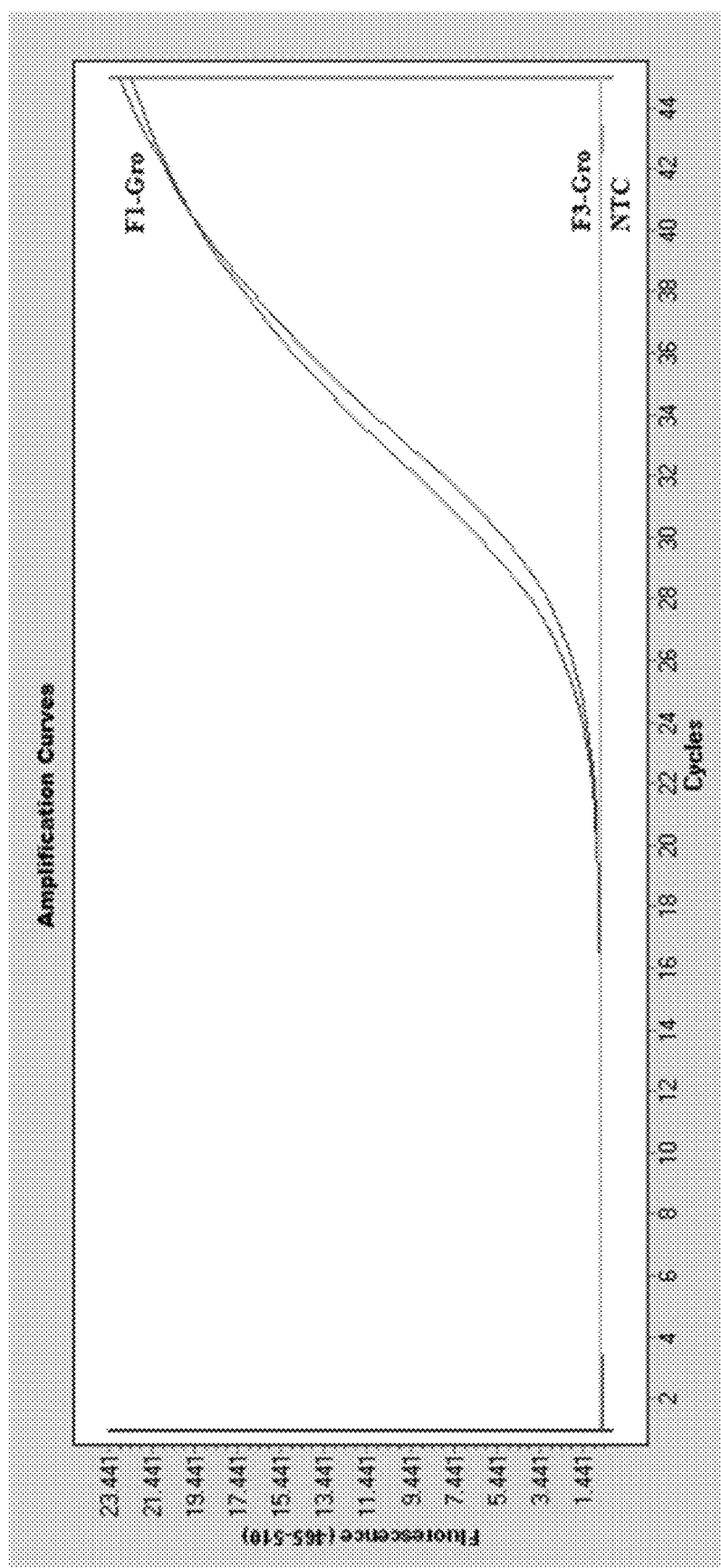

This protocol was replicated and the results obtained successfully proved this method of separation and extraction, as seen in FIGS. 8A through 8C. FIGS. 8A through 8C depict that results obtained from the first trial of the added $3^{rd}$ post-lysozyme filter on the F2→F3 portion were successful in diminishing *E. coli* residual DNA in the F3 portion to zero. The human DNA recover was observed to be much lower than previous analyses.

Figure 9A:
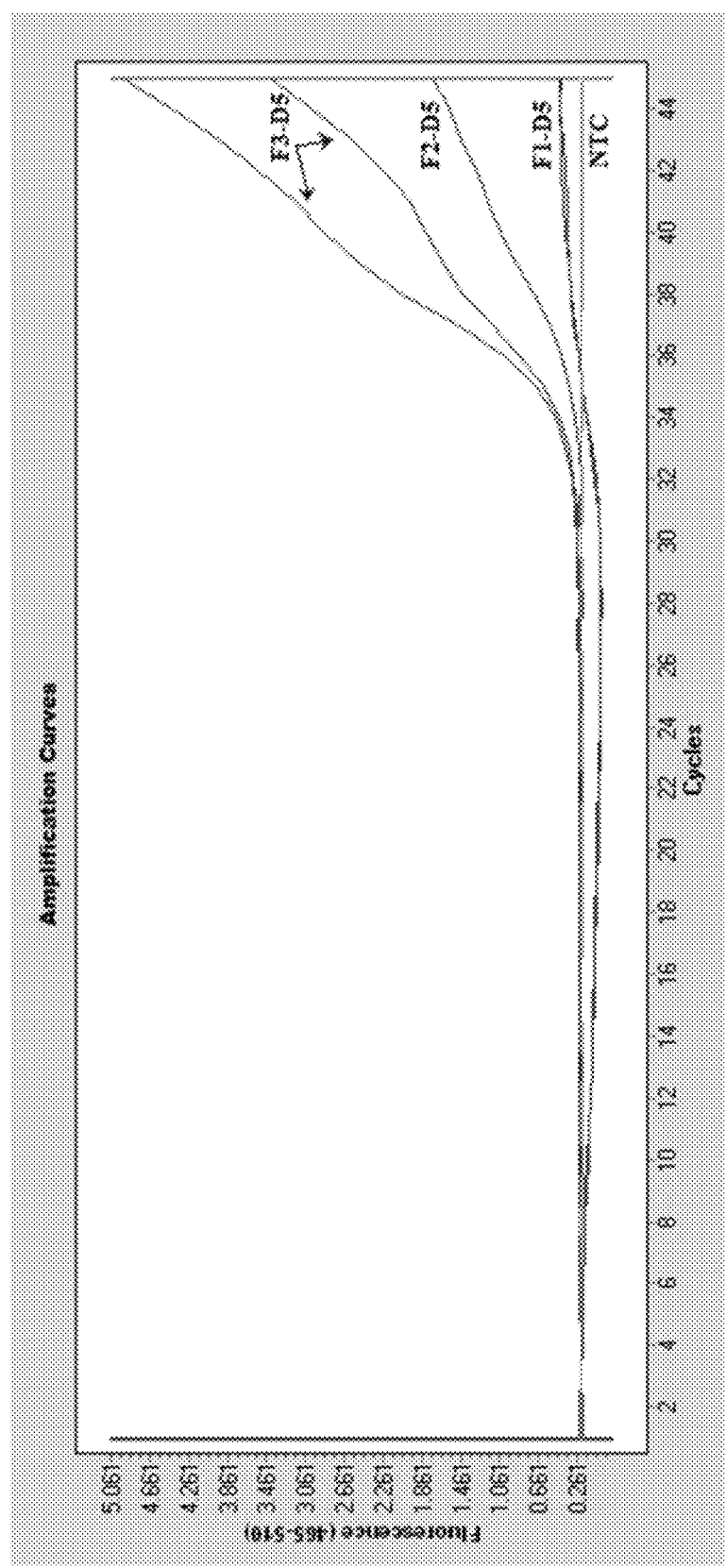
FIGS. 9A and 9B are graphs showing qPCR analysis of a 3-filter method with F2 extraction.
Figure 9B:
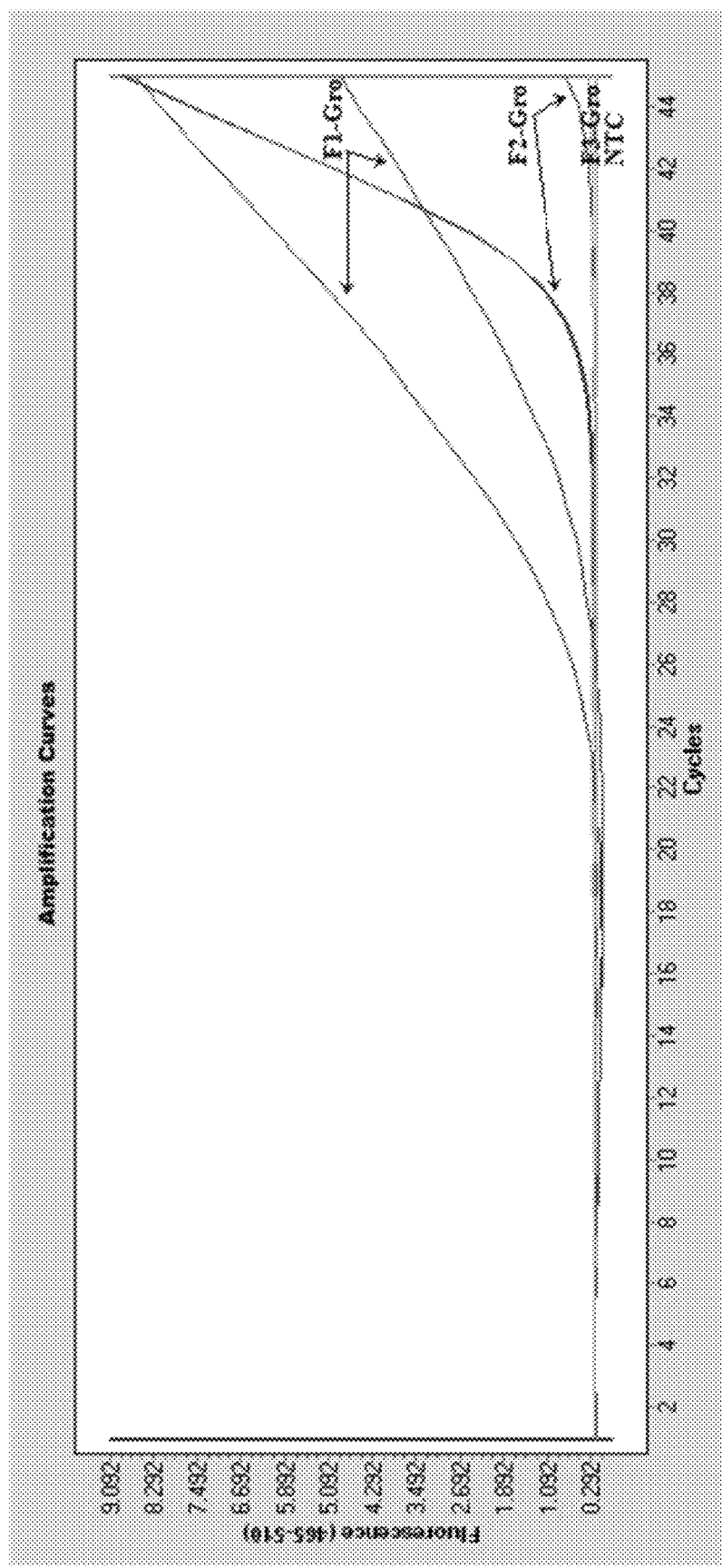

The epithelial "F2" qPCR data was still showing a lower recovery than the stock concentration and pointed to a loss of epithelial DNA during the process. To understand the DNA loss, we decided to extract and co-amplify the "F1" portion of the 3rd post-lysozyme filter that was saved but not extracted. This filtrate showed that a significant portion of the epithelial cells were getting through the 3rd filter, as seen in FIG. 9. FIG. 9 shows that the loss of human DNA in the protocol with the $3^{rd}$ post-lysozyme filter was found in the F2 portion that had been previously set aside and not extracted (FIG. 9A). The F2 portion was observed to have some residual *E. coli* DNA while the F3 portion did not show any residual DNA as expected (FIG. 9B).

During the comparison procedure of different lysis buffers for unfiltered epithelial cells that underwent silica column extraction, the highest quantitation data was observed for the combination of AL Buffer and SDS (2% and 10%) before the Pro K incubation step. The 3-filter protocol was repeated with the addition of the AL Buffer in the re-suspension of the F3 and F2 cellular pellets step and proceeded with the extraction and amplification as replicated previously. The qPCR data for both replicates of the AL Buffer addition in the protocol resulted in almost exactly the same results and Cp values for all samples. Therefore, it was determined that the addition of AL Buffer was not necessary for a successful separation of bacterial and epithelial cell DNA, and the apparent loss of epithelial DNA was attributed to the cells that flowed through during the 3rd filtration. Overall, the proposed method of separation was successful with no residual DNA in either portion. If it is necessary to recover a higher percentage of the epithelial cell DNA for future studies, it is possible to retain that DNA in the "F1-PL" portion that also contains trace amounts of residual bacterial DNA.

The present invention appears to be the first approach that can successfully demonstrate a viable method of separating *E. coli* and human epithelial cell DNA via size exclusion filtration prior to DNA extraction for the purpose of simplifying downstream applications such as shotgun sequencing interpretation. Mixed biological samples, especially mixtures of human and bacterial DNA, are vast in the environment and the human body. Though there have been developments for the healthcare field for this type of separation, the products that have been introduced are extremely expensive and may not be viable for use outside of medicinal studies.

Previous studies conducted for healthcare purposes determined buccal epithelial cells in nature tend to have a tight adherence to bacterial cells as a mechanism to defend the body against foreign bacterial invasion. This characteristic of the epithelial cells may have attributed to their ability to filter through the 10 μM filter even though their average size is 10× that of the filter pores. Once adhered together, the *E. coli* cells would have been able to pull the epithelial cells through the filter alongside the bacteria. Though the method has successfully proven to separate the human cells with no residual bacterial cells in the F3 portion, it was found that almost half of the recovered epithelial cells were in the F2 portion that also contained residual *E. coli* cells. This method attributed cellular loss to the nature of the adhesion of the cells, but further studies should be conducted to determine if this attribution was in fact that cause of the cell loss in the F3 portion. Another possible contribution to the residual epithelial cells in the F1 portion may be the several vortex steps detailed within the protocol. It was found that fewer epithelial cells got through the double 5 μM filter system when a gentle vortex was applied to the sample at each step, as opposed to the vortex speed needed to re-suspend bacterial pellets.

During the 10 μM and 5 μM Celltrics® filter comparison, we found that the initial quantitation with the NanoDrop 2000 showed virtually no residual *E. coli* in the F2 portion, especially with the 10 μM filters. However, when we proceeded with the DNA extraction and amplification, the qPCR data depicted a much higher concentration of residual *E. coli* DNA. We utilized the A600 absorbance to calculate the amount of cells/mL and all readings from the 10 μM filter gave a negative reading, which we attributed to zero residual *E. coli*. The 5 μM filter A600 readings gave a range of 0.000-0.004, which when calculated gave a range of $4.0 \times 10^5$-$2.8 \times 10^6$ cells/mL. This accounted for the difference in expected and actual residual *E. coli* DNA in the F2 and F3 portions. The observed difference in residual *E. coli* DNA between the 10 μM and 5 μM filters was attributed to a small portion being on the filters that were cut up and added to the F2 and F3 portions, as well as the likelihood of bacterial cells being on top of epithelial cells that were not filtered through. Once the F2 and F3 portions were incubated with the bacterial lysis buffer, we observed all *E. coli* flowing through the $3^{rd}$ filter and no residual in the F3 portion.

A preliminary comparison study was conducted of 5 μM Pluristrainer® filters, which are roughly double the surface area of the Celltrics® filters, and the results obtained showed much better separation results for the pre-extraction double filtration method. From stock epithelial counts, found prior to filtration, it was calculated that the expected number of cells was 15. After filtration, 10 cells were observed and counted in the F2 portion. No cells were found in any other sample. Thus, the epithelial cells were completely separated from *E. coli* cells. Therefore, it may be concluded that surface area of the filter used in the method may contribute to the results obtained and may aid in the possible stacking of bacterial cells in human cells during the procedure. Future studies could be conducted to gain a better understanding of the effect of surface area of the filter. For the purpose of this study, the Celltrics® filters were chosen due to cost and sterilization options. It is imperative in research to avoid contamination of valuable samples, so sterility is a key factor in choosing the right tools to use. Development of a contained double-filter system is pending, where future research of filter surface area could be studied further.

When conducting different DNA extraction protocols to determine the highest yield of epithelial cell DNA, the modified Qiagen buccal swab extraction protocol was compared to the published Qiagen extraction protocol for the DSP MiniKit and found the highest yield from quantitation to be a result of the addition of both AL Buffer and our SDS lysis buffer. This mixture was chosen after optimizing the triple-filter protocol to determine if it were possible to produce a higher yield of recovered epithelial cell DNA post-filtration. The Cp values showed no difference between the recovered DNA with or without the added buffer. Therefore, it was determined that the addition of AL Buffer was not necessary for a successful separation of bacterial and epithelial cell DNA, and the apparent loss of epithelial DNA was attributed to the cells that flowed through during the 3rd filtration. Overall, the proposed method of separation was successful with no residual DNA in either portion. If it is necessary to recover a higher percentage of the epithelial cell DNA for future studies, it is possible to retain that DNA in the F2 portion that also contains trace amounts of residual bacterial DNA.

The present invention represents the first successful application of size exclusion combined with differential chemical lysis allowing for separation of bacterial and human epithelial DNA prior to extraction in a cost-effective manner that will maintain cell or DNA viability for downstream applications. The method of the present invention is useful for numerous fields within the scientific research community and will allow labs of varying budgets to utilize this separation easily without compromising time. As the research on the human microbiome and bacteria in general develop in the scientific community, researchers have the ability to learn an incredible amount of new and vital information that could be useful to fields such as environmental studies and remediation, improvement of healthcare with probiotics, forensic science and national security, and others. Moreover, as the wealth of information on bacteria and biological mixtures has grown, so has the need for a simple and cost-efficient method to separate species at the kingdom level without loss of cells or cellular integrity.

What is claimed is:

1. A method of processing a mixture of bacterial cells, plant cells, and animal cells prior to sequencing, comprising the steps of:
    obtaining a tissue sample containing a plurality of bacterial cells, a plurality of plant cells and a plurality of animal cells;
    forming a mixed solution of bacterial, plant and animal cells by combining the tissue sample with a first amount of phosphate-buffered saline in a vessel so that the plurality of bacterial cells, plurality of plant cells and the plurality of animal cells are in suspension;
    filtering the mixed solution a first time using a first wetted filter into a first centrifuge tube to separate a first residue from a first filtrate prior to performing any lysing of the mixed solution of bacterial, plant and animal cells;
    filtering the first filtrate a second time into the first centrifuge tube using a second wetted filter to separate a second residue from a second filtrate;
    washing the first residue from the first wetted filter with a second amount of phosphate-buffered saline into a first collection tube;
    washing the second residue from the second wetted filter with a third amount of phosphate-buffered saline into the first collection tube;
    centrifuging the first wetted filter, the second wetted filter, the first residue, and the second residue in a second centrifuge tube to form a first pellet including only a first type of cells from the plurality of bacterial cells, the plurality of plant cells and the plurality of animal cells;
    centrifuging the first centrifuge tube to form a second pellet including only a second type of cells from the plurality of bacterial cells, the plurality of plant cells and the plurality of animal cells that is different than the first type of cells;
    forming a first suspension of the first pellet in a first lysis solution;
    forming a second suspension of the second pellet in a second lysis solution;
    filtering the first suspension with a third wetted filter to separate a third residue from a third filtrate; and
    washing the third residue from the third wetted filter into a second collection tube, wherein the third residue includes only a third type of cells from the plurality of bacterial cells, the plurality of plant cells and the plurality of animal cells that is different than the first type of cells and the second type of cells.

2. The method of claim 1, wherein the first wetted filter has a pore size of 5 μm.

3. The method of claim 2, wherein the second wetted filter has a pore size of 5 μm.

4. The method of claim 3, wherein the third wetted filter has a pore size of 5 μm.

5. The method of claim 4, wherein the first amount of phosphate-buffered saline comprises 250 μL.

6. The method of claim 5, wherein the second amount of phosphate-buffered saline comprises 250 μL.

7. The method of claim 6, wherein the third amount of phosphate-buffered saline comprises 250 μL.

8. The method of claim 7, wherein the first wetted filter and the second wetted filter are each cut into four equal pieces prior to centrifuging.

9. The method of claim 8, wherein the first lysis solution comprises a 2 percent sodium dodecyl sulfate lysis buffer.

10. The method of claim 9, wherein the second lysis solution comprises a 2 percent sodium dodecyl sulfate lysis buffer.

11. The method of claim 10, further comprising step of incubating the first suspension of the first pellet in the first lysis solution for a first predetermined time period at a first predetermined temperature.

12. The method of claim 11, further comprising step of incubating the second suspension of the second pellet in the second lysis solution for a second predetermined time period at a second predetermined temperature.

* * * * *